United States Patent
Yoshimori

(10) Patent No.: US 11,490,784 B2
(45) Date of Patent: Nov. 8, 2022

(54) ENDOSCOPE APPARATUS

(71) Applicant: FUJIFILM Corporation, Tokyo (JP)

(72) Inventor: Yu Yoshimori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 291 days.

(21) Appl. No.: 16/788,916

(22) Filed: Feb. 12, 2020

(65) Prior Publication Data

US 2020/0260932 A1 Aug. 20, 2020

(30) Foreign Application Priority Data

Feb. 20, 2019 (JP) .............................. JP2019-028362

(51) Int. Cl.
*A61B 1/00* (2006.01)
*A61B 1/045* (2006.01)
(Continued)

(52) U.S. Cl.
CPC ...... *A61B 1/00009* (2013.01); *A61B 1/00045* (2013.01); *A61B 1/00096* (2013.01);
(Continued)

(58) Field of Classification Search
CPC ............ A61B 1/00009; A61B 1/00045; A61B 1/00096; A61B 1/045; A61B 1/0676; A61B 1/00006; A61B 1/05; A61B 1/07; A61B 1/00174; A61B 1/0623; G01B 11/02; G01B 11/14; G01B 9/02; G01B 11/2441;
(Continued)

(56) References Cited

U.S. PATENT DOCUMENTS 4,980,763 A * 12/1990 Lia .................. G01B 11/02
348/137
5,436,655 A * 7/1995 Hiyama ............. A61B 1/00193
348/139
(Continued)

FOREIGN PATENT DOCUMENTS

JP H04145313 * 5/1992
JP H 07136101 * 5/1995
(Continued)

OTHER PUBLICATIONS

The extended European search report issued by the European Patent Office dated Jun. 22, 2020, which corresponds to European Patent Application No. 20155502.6-1122 and is related to U.S. Appl. No. 16/788,916.

*Primary Examiner* — Timothy J Neal
*Assistant Examiner* — Sung Ham
(74) *Attorney, Agent, or Firm* — Studebaker & Brackett PC

(57) ABSTRACT

A position specifying section obtains an observation distance by specifying the position of an irradiated region from a picked-up image that is obtained from the image pickup of a subject on which the irradiated region is formed by auxiliary measurement light. An image processing section sets the amount of offset, which corresponds to a height of the irradiated region of a convex portion of the subject, for the observation distance, and generates an offset measurement marker on the basis of the offset distance that obtained by adding the amount of offset to the observation distance. A specific image in which the offset measurement marker is superimposed on the picked-up image is displayed on a display unit.

10 Claims, 20 Drawing Sheets

(51) Int. Cl.
*A61B 1/06* (2006.01)
*G01B 11/02* (2006.01)
*G01B 11/14* (2006.01)

(52) U.S. Cl.
CPC ............ *A61B 1/045* (2013.01); *A61B 1/0676* (2013.01); *G01B 11/02* (2013.01); *G01B 11/14* (2013.01)

(58) Field of Classification Search
CPC ............ G01B 11/0608; G01B 9/02002; G01B 2210/56; G02B 23/2461; G01N 21/93; G01N 21/954; G01N 2021/95646
See application file for complete search history.

(56) References Cited

U.S. PATENT DOCUMENTS

| | | | |
|---|---|---|---|
| 6,369,401 B1 * | 4/2002 | Lee | G01B 11/00 250/559.21 |
| 2002/0191074 A1 | 12/2002 | Ogawa | |
| 2010/0265251 A1 | 10/2010 | Vining et al. | |
| 2011/0118596 A1 | 5/2011 | Vining et al. | |
| 2012/0105612 A1 * | 5/2012 | Yoshino | A61B 1/00163 348/65 |
| 2016/0014328 A1 * | 1/2016 | Rokutanda | A61B 1/00188 348/65 |
| 2016/0109227 A1 | 4/2016 | Ser et al. | |
| 2019/0204069 A1 | 7/2019 | Tatsuta et al. | |
| 2020/0107698 A1 | 4/2020 | Tatsuta et al. | |
| 2021/0121053 A1 * | 4/2021 | Sidlesky | G01B 11/02 |

FOREIGN PATENT DOCUMENTS

WO 2018051680 A1 3/2018
WO 2019/017018 A1 1/2019

* cited by examiner

FIG. 11

| OBSERVATION IMAGE | SPECIFIC IMAGE (WITHOUT OFFSET SETTING) | SPECIFIC IMAGE (AMOUNT OF OFFSET OF 2 mm) |
|---|---|---|
| CENTRAL COORDINATE: (X2, Y2)<br>RADIUS: r2 | CENTRAL COORDINATE: (X2, Y2)<br>RADIUS: r2 | CENTRAL COORDINATE: (X2, Y2)<br>RADIUS: r2 |
| OBSERVATION DISTANCE D5: 5 mm | OBSERVATION DISTANCE D5: 5 mm | OBSERVATION DISTANCE D6: 7 mm |
| (WITHOUT MARKER) | MEASUREMENT MARKER: DIAMETER OF 5 mm (FOR OBSERVATION DISTANCE OF 5 mm) | OFFSET MEASUREMENT MARKER: DIAMETER OF 5 mm (OFFSET MEASUREMENT MARKER FOR OBSERVATION DISTANCE OF 7 mm) |

FIG. 12

| SPECIFIC IMAGE (WITHOUT OFFSET SETTING) | | |
|---|---|---|
| 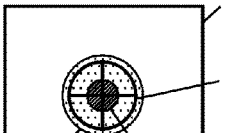 | 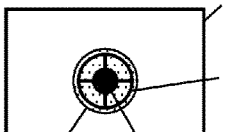 | 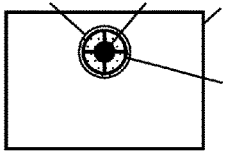 |
| CENTRAL COORDINATE: (X1, Y1)<br>RADIUS: r3 | CENTRAL COORDINATE: (X2, Y2)<br>RADIUS: r4 | CENTRAL COORDINATE: (X3, Y3)<br>RADIUS: r5 |
| OBSERVATION<br>DISTANCE D5: 5 mm | OBSERVATION<br>DISTANCE D5: 7 mm | OBSERVATION<br>DISTANCE D5: 9 mm |
| MEASUREMENT MARKER:<br>DIAMETER OF 5 mm<br>(FOR OBSERVATION<br>DISTANCE OF 5 mm) | MEASUREMENT MARKER:<br>DIAMETER OF 5 mm<br>(FOR OBSERVATION<br>DISTANCE OF 7 mm) | MEASUREMENT MARKER:<br>DIAMETER OF 5 mm<br>(FOR OBSERVATION<br>DISTANCE OF 9 mm) |

| SPECIFIC IMAGE (WITH OFFSET SETTING: AMOUNT OF OFFSET OF 2mm) | |
|---|---|
| 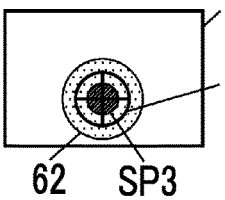 | 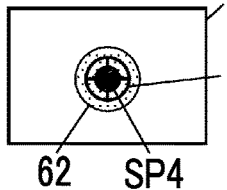 |
| CENTRAL COORDINATE: (X1, Y1)<br>RADIUS: r3 | CENTRAL COORDINATE: (X2, Y2)<br>RADIUS: r4 |
| OBSERVATION DISTANCE D5: 5 mm | OBSERVATION DISTANCE D5: 7 mm |
| OFFSET MEASUREMENT MARKER:<br>DIAMETER OF 5 mm<br>(MEASUREMENT MARKER FOR<br>OBSERVATION DISTANCE OF 7 mm) | OFFSET MEASUREMENT MARKER:<br>DIAMETER OF 5 mm<br>(MEASUREMENT MARKER FOR<br>OBSERVATION DISTANCE OF 9 mm) | x (PIXEL POSITION OF SPOT IN X DIRECTION)

y (PIXEL POSITION OF SPOT IN Y DIRECTION)

x (PIXEL POSITION OF SPOT IN X DIRECTION)

y (PIXEL POSITION OF SPOT IN Y DIRECTION)

ENDOSCOPE APPARATUS

CROSS-REFERENCE TO RELATED APPLICATIONS

This application claims priority under 35 U.S.C. § 119(a) to Japanese Patent Application No. 2019-028362 filed on Feb. 20, 2019. The above application is hereby expressly incorporated by reference, in its entirety, into the present application.

BACKGROUND OF THE INVENTION

1. Field of the Invention

The present invention relates to an endoscope apparatus that measures the size of a subject.

2. Description of the Related Art

A distance to an object to be observed, the size of an object to be observed, or the like is acquired in an endoscope apparatus. For example, WO2018/051680A (corresponding to US2019/0204069A1) discloses an endoscope apparatus system that irradiates a subject with auxiliary measurement light and causes a display device to display an index figure having a set size together with the image of the subject according to the position of a spot formed on an image pickup element by auxiliary measurement light.

SUMMARY OF THE INVENTION

However, in the related art, there is a concern that a figure or the index of gradations having a size different from an actual size may be displayed in a case where the surface of the subject includes a concave/convex portion, such as a polyp. The reason for this is that an irradiation position where a spot is formed on the subject by auxiliary measurement light in a case where the concave/convex portion formed on the surface of the subject is irradiated with auxiliary measurement light is shifted from an irradiation position in a case where there is no concave/convex portion.

In contrast, a method of displaying an index, which is to be obtained in a case where a spot is formed at the concave/convex portion by auxiliary measurement light, using data where the position of auxiliary measurement light and an index are calibrated according to the concave/convex portion formed on the surface of the subject is thought. However, since actual concave/convex portions are various, calibration needs to be performed for every concave/convex portion. Accordingly, there is a concern that work may be complicated in this method.

The invention has been made in consideration of the above-mentioned circumstances, and an object of the invention is to provide an endoscope apparatus that can simply measure a value closer to an actual value even in a case where a convex portion of a subject is irradiated with auxiliary measurement light.

To solve the problems in the related art, an aspect of the invention provides an endoscope apparatus comprising: an illumination light source unit that emits illumination light used to illuminate a subject; an auxiliary measurement light source unit that emits auxiliary measurement light; an image acquisition unit that acquires a picked-up image obtained from image pickup of the subject which is illuminated with the illumination light and on which an irradiated region is formed by the auxiliary measurement light; a position specifying section that specifies a position of the irradiated region from the picked-up image; a distance calculation section that obtains an observation distance, which is a distance between an endoscope-distal end part and the subject, from the position of the irradiated region; an offset setting section that sets an amount of offset, which corresponds to a height of the irradiated region of a convex portion, for the observation distance; an offset distance-calculation section that calculates an offset distance by adding the amount of offset to the observation distance; an offset measurement marker-generation section that generates an offset measurement marker on the basis of the offset distance; and a display control unit that displays a specific image in which the offset measurement marker is superimposed on the picked-up image.

It is preferable that the height of the irradiated region of the convex portion is a distance between the irradiated region of the convex portion and a flat portion of the convex portion in a vertical direction.

It is preferable that the endoscope apparatus further comprises an offset input receiving section receiving an input of the amount of offset and the offset setting section sets the amount of offset by using the input of the amount of offset received by the offset input receiving section.

It is preferable that the amount of offset is manually input.

It is preferable that the endoscope apparatus further comprises an automatic offset-amount determination section automatically determining the amount of offset and the offset setting section sets the amount of offset by using the amount of offset determined by the automatic offset-amount determination section.

It is preferable that the endoscope apparatus further comprises a specific light source unit emitting specific light forming a linear specific region on the subject and a first convex portion-height determination section specifying the specific region of the convex portion of the subject and determining a height of the specific region of the convex portion from the specific region of the convex portion, and the automatic offset-amount determination section determines the amount of offset by using the height of the specific region of the convex portion.

It is preferable that a height of a specific region of the convex portion is a distance between an apex of the convex portion and a flat portion of the convex portion in a vertical direction, the endoscope apparatus further comprises a second convex portion-height determination section specifying a shadow of the convex portion by image analysis using the picked-up image and determining a height of the convex portion from the shadow of the convex portion, and the automatic offset-amount determination section determines the amount of offset by using the height of the irradiated region of the convex portion.

It is preferable that the offset measurement marker-generation section generates a first offset measurement marker, which shows an actual size of the subject, or a second offset measurement marker, which includes a crossing line formed on the subject by the auxiliary measurement light and gradations formed on the crossing line and serving as an index of a size of the subject.

It is preferable that the endoscope apparatus further comprises an offset measurement marker-selection section receiving selection of the type of the offset measurement marker and the offset measurement marker-generation section generates the offset measurement marker according to the selection received by the offset measurement marker-selection section.

It is preferable that the endoscope apparatus further comprises a display unit and the display unit displays the specific image and the amount of offset.

According to the aspect of the invention, it is possible to provide an endoscope apparatus that simply measures a value closer to an actual value even in a case where a convex portion of a subject is irradiated with auxiliary measurement light.

BRIEF DESCRIPTION OF THE DRAWINGS

FIG. 11 is a table illustrating an observation image, a specific image, and a specific image in which an offset is set.

FIG. 12 is a table illustrating the amount of offset.

DESCRIPTION OF THE PREFERRED EMBODIMENTS

Figure 1:
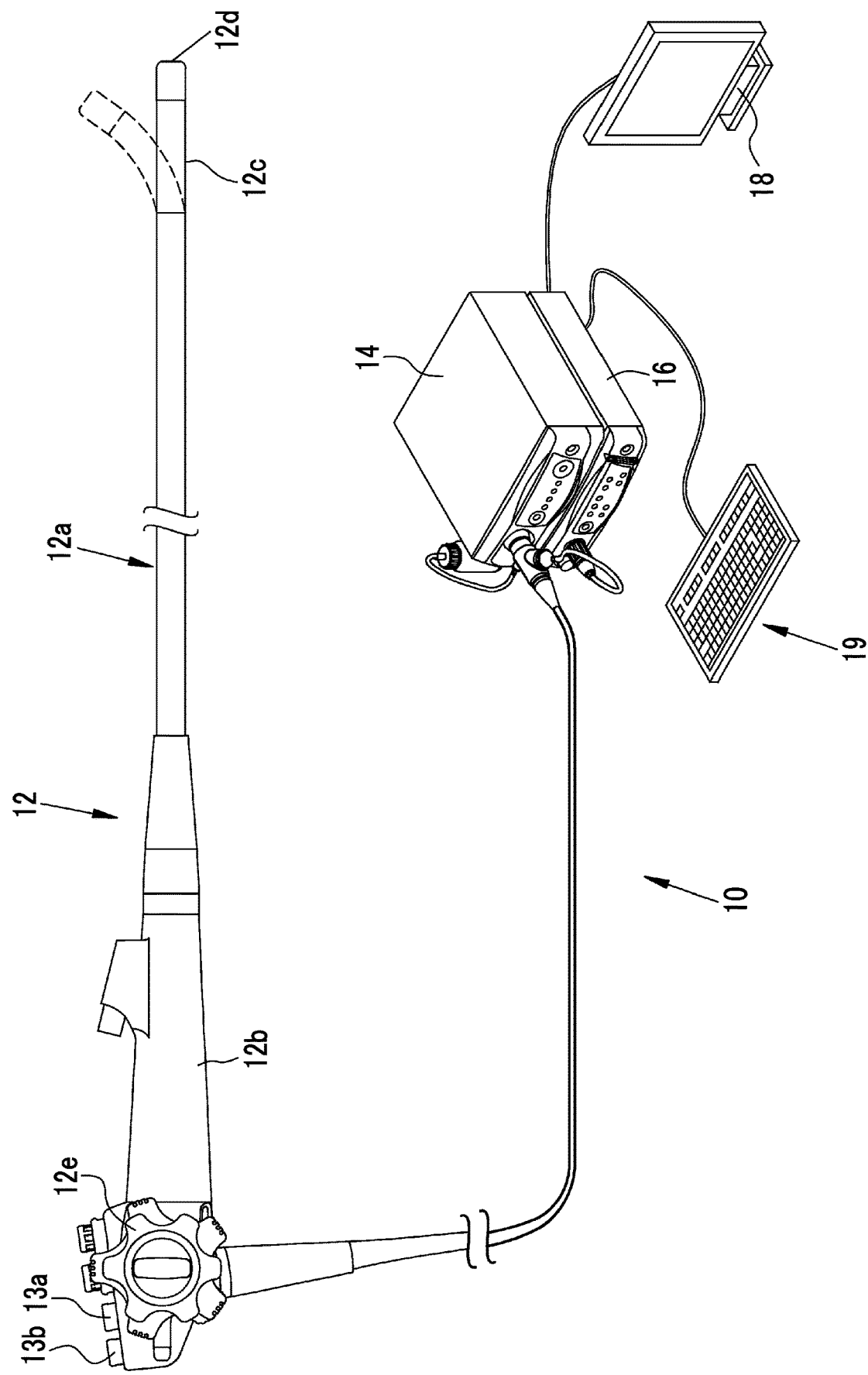
FIG. 1 is a diagram showing the appearance of an endoscope apparatus.

As shown in FIG. 1, an endoscope apparatus 10 includes an endoscope 12, a light source device 14, a processor device 16, a monitor 18, and a user interface 19. The endoscope 12 is optically connected to the light source device 14, and is electrically connected to the processor device 16. The processor device 16 is electrically connected to the monitor 18 (display unit) that displays an image. The user interface 19 is connected to the processor device 16, and is used for various setting operations and the like for the processor device 16. The user interface 19 includes a mouse and the like addition to a keyboard shown in FIG. 1.

The endoscope 12 includes an insertion part 12a that is to be inserted into an object to be examined, an operation part 12b that is provided at a proximal end portion of the insertion part 12a, and a bendable part 12c and a distal end part 12d that are provided on the distal end side of the insertion part 12a. The bendable part 12c operates to be bent by the operation of angle knobs 12e of the operation part 12b. The distal end part 12d is made to face in a desired direction by the bending operation of the bendable part 12c.

The endoscope 12 has a normal mode and a length measurement mode, and these two modes are switched by a mode changeover switch 13a that is provided on the operation part 12b of the endoscope 12. The normal mode is a mode where a picked-up image obtained from the image pickup of an object to be observed illuminated with illumination light is displayed. Accordingly, a measurement marker is not displayed in the normal mode. The length measurement mode is a mode where an object to be observed is illuminated with illumination light and auxiliary measurement light and a measurement marker to be used to measure the size of the object to be observed or the like is displayed in a picked-up image obtained from the image pickup of the object to be observed. Auxiliary measurement light is light that is used to measure a subject.

Further, the operation part 12b of the endoscope 12 is provided with a freeze switch 13b (static image-acquisition instruction unit) that is used to give a static image-acquisition instruction to acquire the static image of a picked-up image. In a case where a user operates the freeze switch 13b, the screen of the monitor 18 is frozen and displayed and an alert sound (for example, "beep") informing the acquisition of a static image is generated together. Then, the static images of the picked-up image, which are obtained before and after the operation timing of the freeze switch 13b, are stored in a static image storage unit 37 (see FIG. 3) provided in the processor device 16. Furthermore, it is preferable that measurement information to be described later is also stored together with the static image of the picked-up image in a case where the endoscope 12 is set to the length measurement mode. The static image storage unit 37 is a storage unit, such as a hard disk or a universal serial bus (USB)

memory. In a case where the processor device 16 can be connected to a network, the static image of the picked-up image may be stored in a static image storage server (not shown), which is connected to a network, instead of or in addition to the static image storage unit 37.

A static image-acquisition instruction may be given using an operation device other than the freeze switch 13*b*. For example, a foot pedal may be connected to the processor device 16, and a static image-acquisition instruction may be given in a case where a user operates the foot pedal (not shown) with a foot. A static image-acquisition instruction may be given by a foot pedal that is used to switch a mode. Further, a gesture recognition unit (not shown), which recognizes the gestures of a user, may be connected to the processor device 16, and a static image-acquisition instruction may be given in a case where the gesture recognition unit recognizes a specific gesture of a user. The gesture recognition unit may also be used to switch a mode.

Furthermore, a visual line input unit (not shown), which is provided close to the monitor 18, may be connected to the processor device 16, and a static image-acquisition instruction may be given in a case where the visual line input unit recognizes that a user's visual line is in a predetermined region of the monitor 18 for a predetermined time or longer. Further, a voice recognition unit (not shown) may be connected to the processor device 16, and a static image-acquisition instruction may be given in a case where the voice recognition unit recognizes a specific voice generated by a user. The voice recognition unit may also be used to switch a mode. Furthermore, an operation panel (not shown), such as a touch panel, may be connected to the processor device 16, and a static image-acquisition instruction may be given in a case where a user makes a specific operation on the operation panel. The operation panel may also be used to switch a mode.

Figure 2:
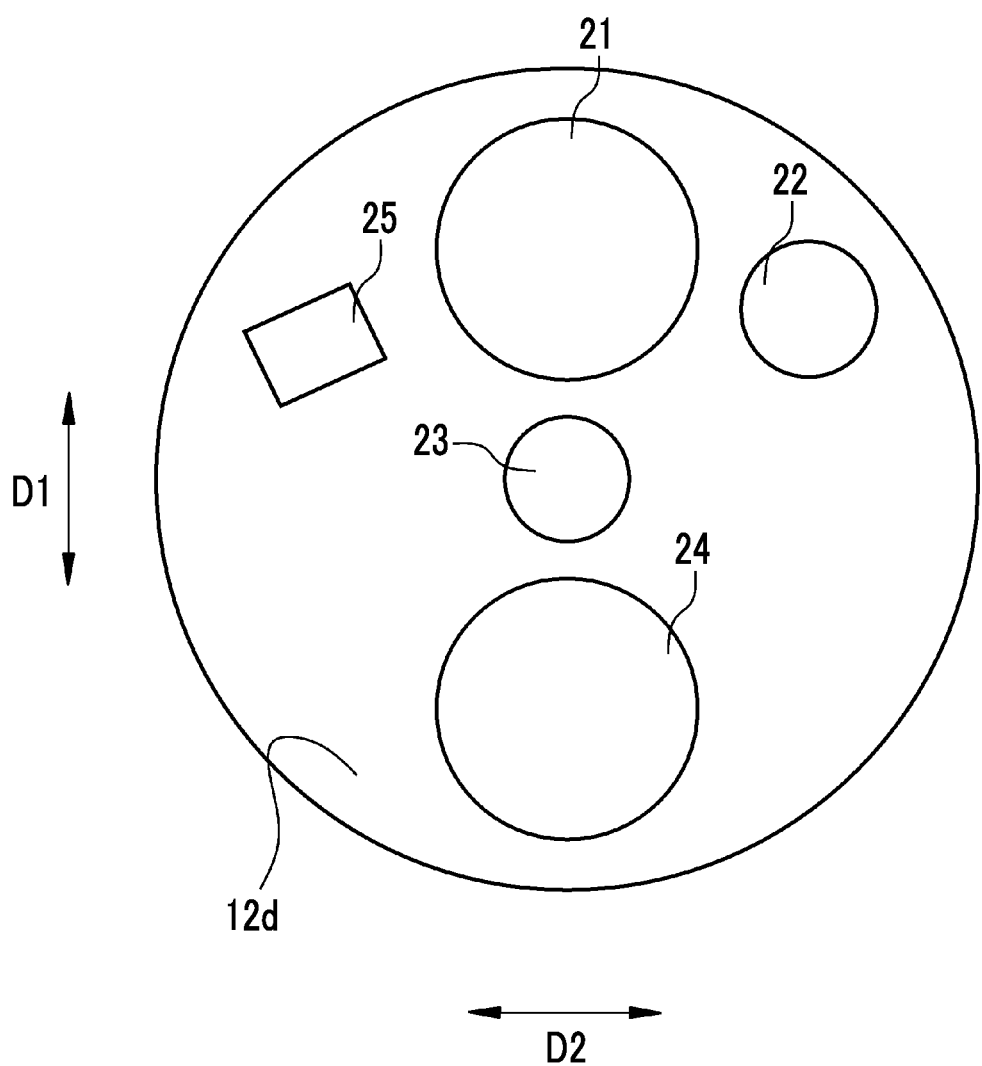
FIG. 2 is a plan view of a distal end part of an endoscope.

As shown in FIG. 2, the distal end part 12*d* of the endoscope 12 (hereinafter, referred to as an endoscope-distal end part 12*d*) has a substantially circular shape; and is provided with an objective lens 21 that is positioned closest to a subject among optical members of an image pickup optical system of the endoscope 12, an illumination lens 22 that is used to irradiate a subject with illumination light, an auxiliary measurement lens 23 that is used to illuminate a subject with auxiliary measurement light to be described later, an opening 24 that allows a treatment tool to protrude toward a subject, and an air/water supply nozzle 25 that is used to supply air and water.

An optical axis Ax of the objective lens 21 extends in a direction perpendicular to the plane of paper. A vertical first direction D1 is orthogonal to the optical axis Ax, and a horizontal second direction D2 is orthogonal to the optical axis Ax and the first direction D1. The objective lens 21 and the auxiliary measurement lens 23 are arranged in the first direction D1.

Figure 3:
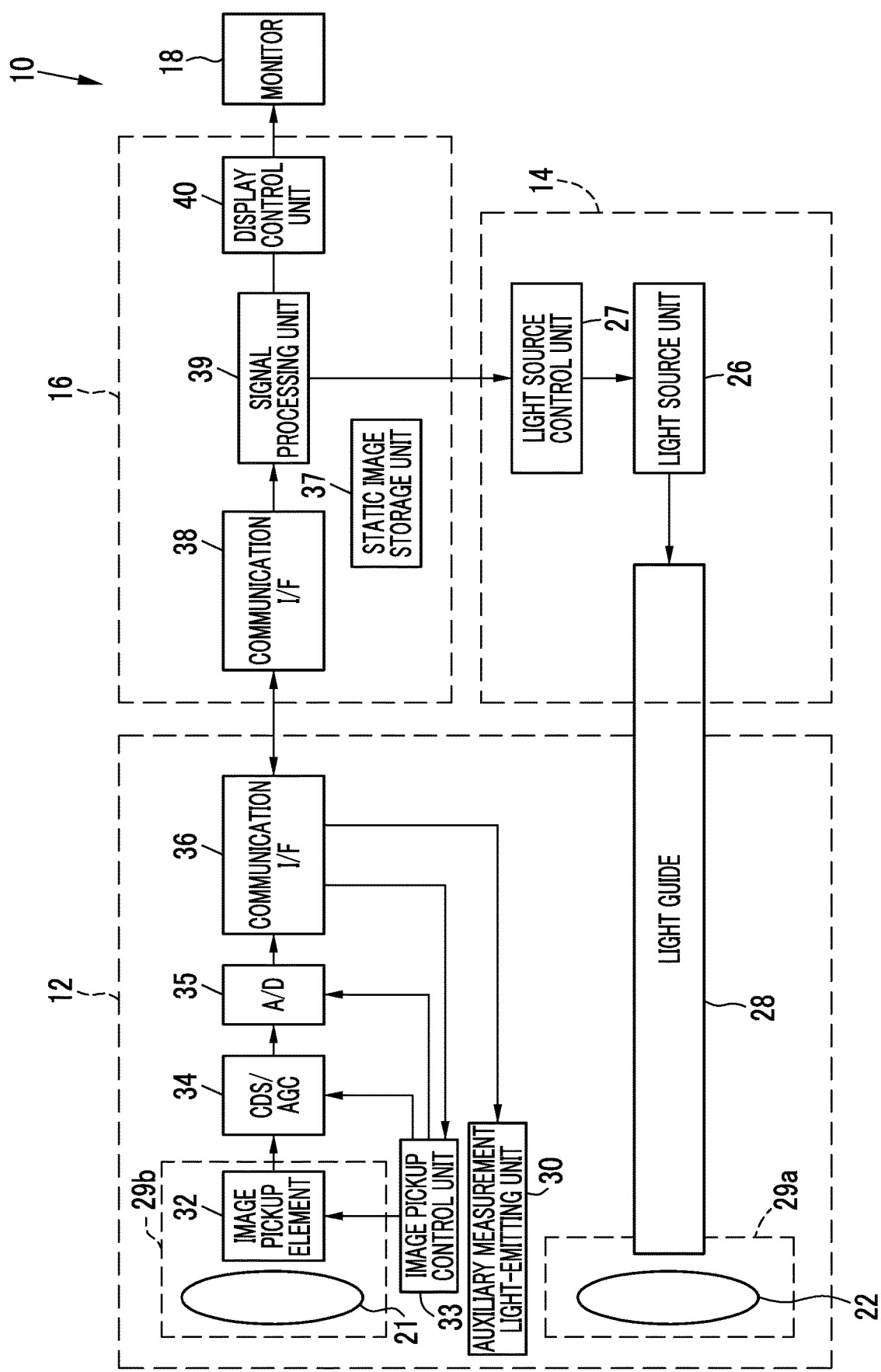
FIG. 3 is a block diagram showing the functions of the endoscope apparatus.

As shown in FIG. 3, the light source device 14 comprises a light source unit 26 and a light source control unit 27. The light source unit 26 (illumination light source unit) generates illumination light that is used to illuminate a subject. Illumination light emitted from the light source unit 26 is incident on a light guide 28, and a subject is irradiated with illumination light through the illumination lens 22. In the light source unit 26, a white light source emitting white light, a plurality of light sources, which includes a white light source and a light source emitting another color light (for example, a blue light source emitting blue light), or the like is used as a light source of illumination light.

An illumination optical system 29*a*, an image pickup optical system 29*b*, and an auxiliary measurement light-emitting unit 30 are provided in the endoscope-distal end part 12*d*. The illumination optical system 29*a* includes the illumination lens 22, and an object to be observed is irradiated with light, which is emitted from the light guide 28, through the illumination lens 22. The image pickup optical system 29*b* includes the objective lens 21 and an image pickup element 32. Light reflected from the object to be observed is incident on the image pickup element 32 through the objective lens 21. Accordingly, the reflected image of the object to be observed is formed on the image pickup element 32.

The image pickup element 32 is a color image pickup sensor, and picks up the reflected image of an object to be examined and outputs image signals. It is preferable that the image pickup element 32 is a charge coupled device (CCD) image pickup sensor, a complementary metal-oxide semiconductor (CMOS) image pickup sensor, or the like. The image pickup element 32 used in the invention is a color image pickup sensor that is used to obtain RGB image signals corresponding to three colors of R (red), G (green), and B (blue). The image pickup element 32 is controlled by an image pickup control unit 33.

The image signals output from the image pickup element 32 are transmitted to a CDS/AGC circuit 34. The CDS/AGC circuit 34 performs correlated double sampling (CDS) or auto gain control (AGC) on the image signals that are analog signals. The image signals, which have been transmitted through the CDS/AGC circuit 34, are converted into digital image signals by an analog/digital converter (A/D converter) 35. The digital image signals, which have been subjected to A/D conversion, are input to the processor device 16 through a communication interface (I/F) 36.

The processor device 16 comprises a communication interface (I/F) 38 that is connected to the communication I/F 36 of the endoscope 12, the static image storage unit 37, a signal processing unit 39, and a display control unit 40. The communication I/F 38 receives the image signals, which are transmitted from the communication I/F 36 of the endoscope 12, and transmits the image signals to the signal processing unit 39. A memory, which temporarily stores the image signals received from the communication I/F 38, is built in the signal processing unit 39, and the signal processing unit 39 processes an image signal group, which is a set of the image signals stored in the memory, to generate the picked-up image. In a case where the endoscope 12 is set to the length measurement mode, the signal processing unit 39 may be adapted to perform structure-emphasis processing for emphasizing structures, such as blood vessels, or color difference-emphasis processing for increasing a color difference between a normal area and a lesion area of the object to be observed on the picked-up image. The display control unit 40 displays the picked-up image, which is generated by the signal processing unit 39, on the monitor 18.

Figure 4:
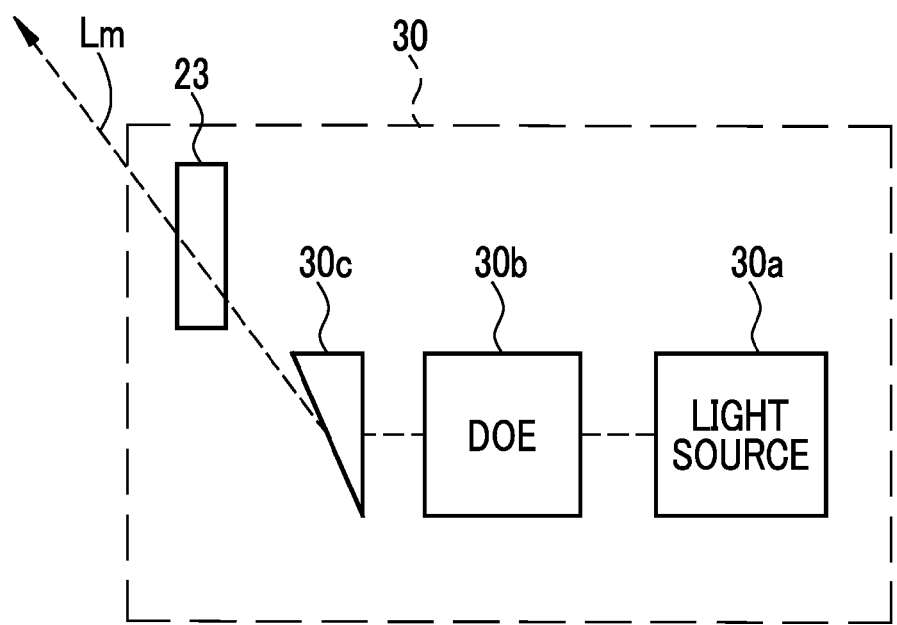
FIG. 4 is a block diagram of an auxiliary measurement light-emitting unit.

As shown in FIG. 4, the auxiliary measurement light-emitting unit 30 (specific light source unit) comprises a light source 30*a*, a diffractive optical element (DOE) 30*b*, a prism 30*c*, and the auxiliary measurement lens 23. The light source 30*a* emits auxiliary measurement light. The light source 30*a* is to emit light having a color that can be detected by pixels of the image pickup element 32 (specifically visible light), and includes a light-emitting element, such as a laser light source LD (laser diode) or a light emitting diode (LED), and a condenser lens that condenses light emitted from the light-emitting element.

It is preferable that light emitted from the light source 30a is red light having a wavelength in the range of, for example, 600 nm to 650 nm. Alternatively, green light having a wavelength in the range of 495 nm to 570 nm may be used. The DOE 30b converts the light, which is emitted from the light source, into auxiliary measurement light that is used to obtain measurement information.

The prism 30c is an optical member that is used to change the travel direction of auxiliary measurement light converted by the DOE 30b. The prism 30c changes the travel direction of auxiliary measurement light so that auxiliary measurement light crosses the visual field of the image pickup optical system including the objective lens 21 and lens groups. The details of the travel direction of auxiliary measurement light will also be described later. A subject is irradiated with auxiliary measurement light, which is emitted from the prism 30c, through the auxiliary measurement lens 23.

Figure 5:
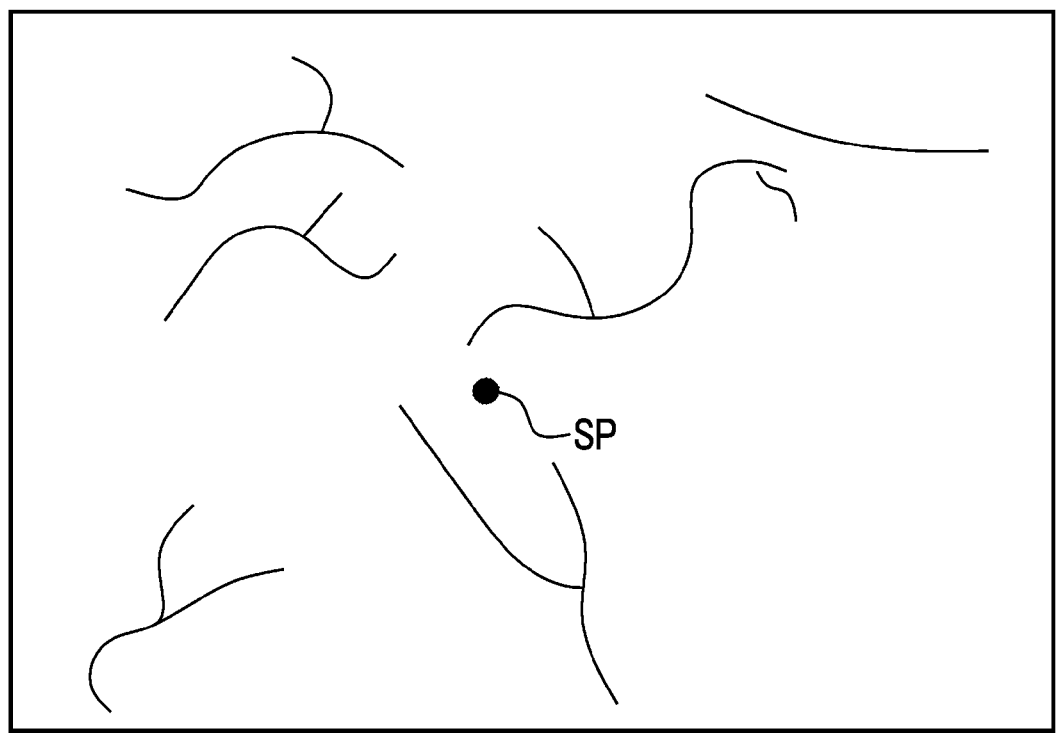
FIG. 5 is a diagram illustrating a spot SP that is formed on a subject by auxiliary measurement light.

In a case where the subject is irradiated with auxiliary measurement light, a spot SP as a circular region is formed on the subject as shown in FIG. 5. That is, the communication I/F 38 that is an image acquisition unit acquires a picked-up image that is obtained from the image pickup of a subject which is illuminated with illumination light and on which the spot SP (irradiated region) is formed by auxiliary measurement light. The position of the spot SP is specified by a position specifying section 50 (see FIG. 7) from the picked-up image that is acquired by the communication I/F 38. An observation distance that is a distance between the endoscope-distal end part 12d and the subject is obtained from the specified position of the spot SP. A measurement marker showing an actual size can be set for the observation distance. Accordingly, a measurement marker showing an actual size is set according to the position of the spot SP. The set measurement marker is displayed in the picked-up image in a case where an offset is not set or the amount of offset is set to 0. Plural kinds of measurement markers, such as a first measurement marker and a second measurement marker, are included in the measurement marker and an offset measurement marker to be described later as described later, and a measurement marker to be displayed in the picked-up image among the plural kinds of measurement markers can be selected according to a user's instruction. For example, the user interface 19 is used for the user's instruction.

An auxiliary measurement slit formed in the endoscope-distal end part 12d may be used instead of the auxiliary measurement lens 23. Further, it is preferable that an anti-reflection coating (AR coating) (anti-reflection portion) is provided on the auxiliary measurement lens 23. The reason why the anti-reflection coating is provided as described above is that it is difficult for a position specifying section 50 to be described later to recognize the position of the spot SP formed on the subject by auxiliary measurement light in a case where auxiliary measurement light is reflected without being transmitted through the auxiliary measurement lens 23 and a ratio of auxiliary measurement light with which a subject is irradiated is reduced.

The auxiliary measurement light-emitting unit 30 has only to be capable of emitting auxiliary measurement light to the visual field of the image pickup optical system. For example, the light source 30a may be provided in the light source device and light emitted from the light source 30a may be guided to the DOE 30b by optical fibers. Further, the prism 30c may not be used and the directions of the light source 30a and the DOE 30b may be inclined with respect to the optical axis Ax so that auxiliary measurement light is emitted in a direction crossing the visual field of the image pickup optical system.

Figure 6:
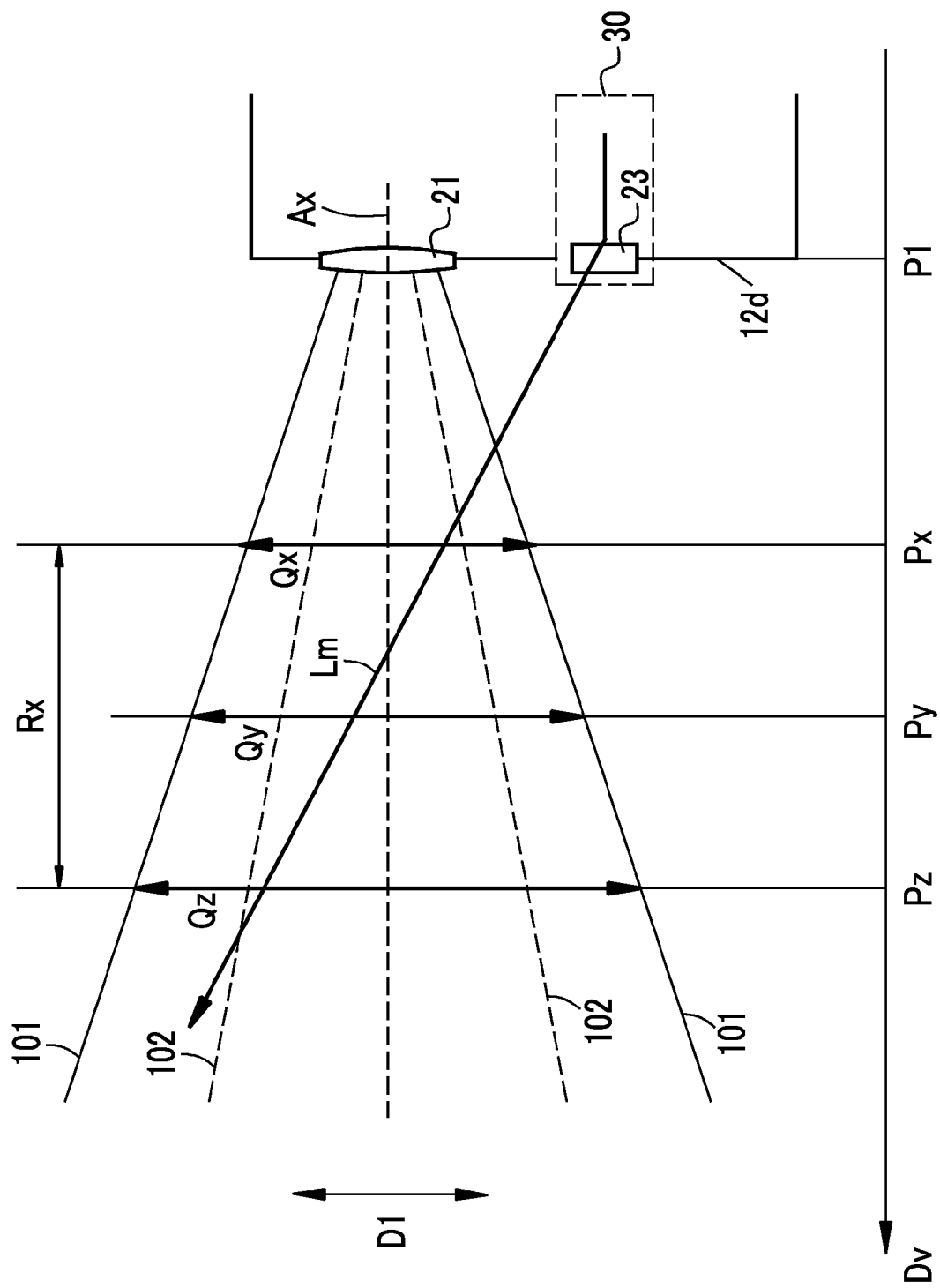
FIG. 6 is a diagram illustrating a relationship between a distal end part of an endoscope and a near end Px, an intermediate vicinity Py, and a far end Pz in a range Rx of an observation distance and a relationship between an optical axis and auxiliary measurement light.

With regard to the travel direction of auxiliary measurement light, auxiliary measurement light is emitted in a state where an optical axis Lm of auxiliary measurement light crosses the optical axis Ax of the objective lens 21 as shown in FIG. 6. In a case where a subject can be observed in a range Rx of the observation distance, it is understood that the positions (points where the respective arrows Qx, Qy, and Qz cross the optical axis Ax) of spots SP formed on the subject by auxiliary measurement light in image pickup ranges (shown by arrows Qx, Qy, and Qz) at a near end Px, an intermediate vicinity Py, and a far end Pz of the range Rx are different from each other. The position of the endoscope-distal end part 12d is referred to as a position P1. The observation distance is a distance between the endoscope-distal end part 12d and the subject. Accordingly, the observation distance is a distance between the position P1 and each of the near end Px, the intermediate vicinity Py, and the far end Pz. In detail, the observation distance is a distance between the subject and a position on the endoscope-distal end part 12d from which the optical axis Ax of the objective lens 21 extends. An axis Dv represents the observation distance. The image pickup angle of view of the image pickup optical system is represented by a region between two solid lines 101, and measurement is performed in a central region (a region between two dotted lines 102), in which an aberration is small, of this image pickup angle of view.

Since auxiliary measurement light is emitted in a state where the optical axis Lm of auxiliary measurement light crosses the optical axis Ax as described above, sensitivity to the movement of the position of the spot with respect to a change in the observation distance is high. Accordingly, the size of the subject can be measured with high accuracy. The image of the subject illuminated with auxiliary measurement light is picked up by the image pickup element 32, so that a picked-up image including the spot SP is obtained. In the picked-up image, the position of the spot SP varies depending on a relationship between the optical axis Ax of the objective lens 21 and the optical axis Lm of auxiliary measurement light and an observation distance. The number of pixels showing the same actual size (for example, 5 mm) is increased in the case of a short observation distance, and the number of pixels showing the same actual size (for example, 5 mm) is reduced in the case of a long observation distance.

Accordingly, in a case where information showing a relationship between the position of the spot SP and measurement information (the number of pixels) corresponding to the actual size of the subject is stored in advance as described in detail later, the measurement information can be calculated from the position of the spot SP.

Figure 7:
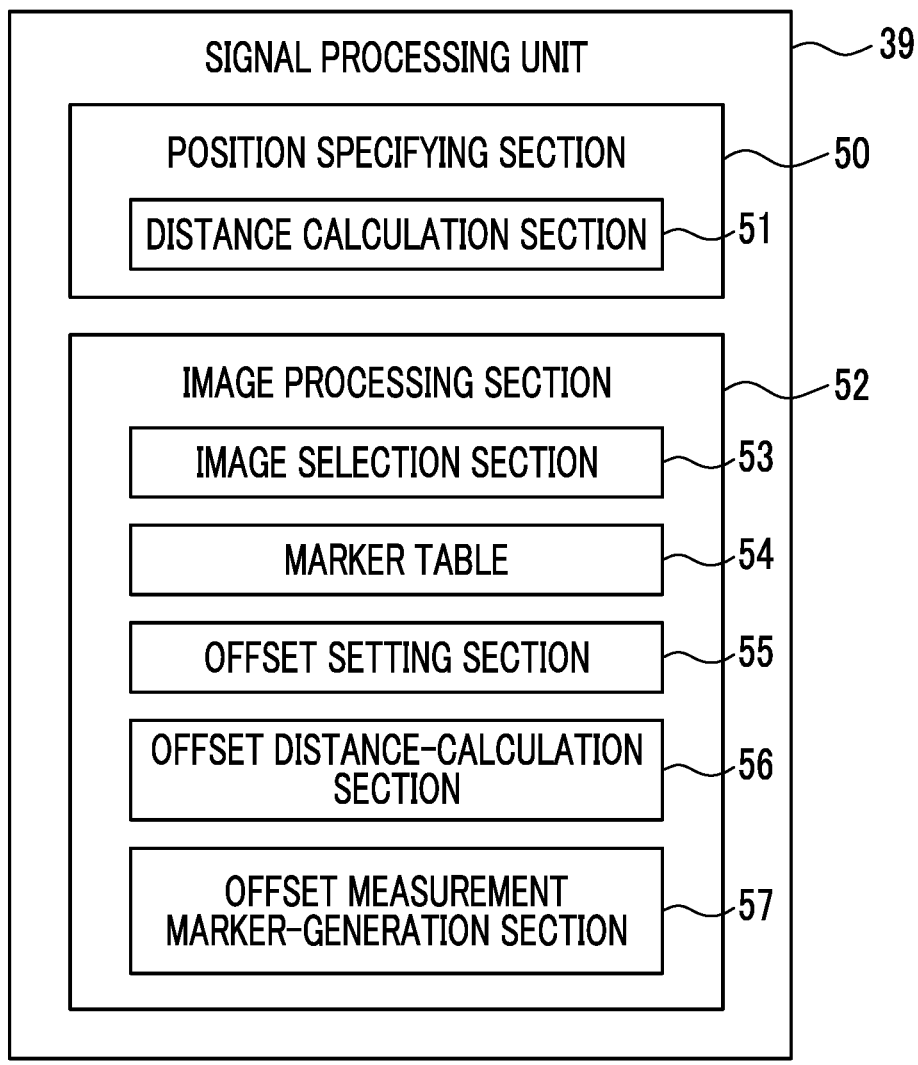
FIG. 7 is a block diagram showing the functions of a signal processing unit.

As shown in FIG. 7, the signal processing unit 39 of the processor device 16 comprises a position specifying section 50 and an image processing section 52 to perform the recognition of the position of the spot SP, the calculation of the observation distance to the subject, and the setting of various measurement markers. The position specifying section 50 specifies the position of the spot SP in the picked-up image and calculates an observation distance, and the image processing section 52 sets various measurement markers on the basis of the observation distance and generates a specific image, which is a processed picked-up image, using the various measurement markers. The specific image is displayed on the monitor 18 by the display control unit 40.

In a case where the endoscope 12 is set to the length measurement mode, the light source unit 26 and the auxiliary measurement light-emitting unit 30 continuously emit illumination light and auxiliary measurement light. In some cases, auxiliary measurement light may be emitted in a state where auxiliary measurement light flickers or dims. The picked-up image is an RGB image corresponding to three colors, but may be other color images (a luminance signal Y and color difference signals Cr and Cb). Accordingly, in a case where the endoscope 12 is set to the length measurement mode, the picked-up image of the subject illuminated with illumination light and auxiliary measurement light is input to the signal processing unit 39. The picked-up image is acquired by the communication I/F 38 (image acquisition unit).

In a case where the endoscope 12 is set to the normal mode, the light source unit 26 always emits illumination light. The subject is irradiated with illumination light through the light guide 28. The light source 30a of the auxiliary measurement light-emitting unit 30 stops in the normal mode. Accordingly, in a case where the endoscope 12 is set to the normal mode, the picked-up image of the subject illuminated with illumination light is input to the signal processing unit 39. The picked-up image is acquired by the communication I/F 38 (image acquisition unit).

The position specifying section 50 includes a distance calculation section 51. The position specifying section 50 specifies the position of the spot SP on the basis of the picked-up image of the subject that is illuminated with illumination light and auxiliary measurement light in the length measurement mode. The distance calculation section 51 obtains an observation distance from the position of the spot SP.

The image processing section 52 includes an image selection section 53, a marker table 54, an offset setting section 55, an offset distance-calculation section 56, and an offset measurement marker-generation section 57. The image processing section 52 performs processing for generating a specific image in which an offset measurement marker is superimposed on the picked-up image. The image selection section 53 selects the picked-up image obtained in the length measurement mode, which is an image to be subjected to processing based on the position of the spot SP, between the picked-up image obtained in the normal mode and the picked-up image obtained in the length measurement mode. The marker table 54 is a table in which information representing a relationship between an observation distance corresponding to the position of the spot SP and measurement information (the number of pixels) corresponding to the actual size of a subject is stored in advance. The offset setting section 55 sets the amount of offset, which corresponds to the height of the spot SP of a convex portion, for an observation distance. The offset distance-calculation section 56 calculates an offset distance by adding the amount of offset to the observation distance. The offset measurement marker-generation section 57 generates an offset measurement marker on the basis of the offset distance.

An offset will be described below. First, a convex portion of a subject means a portion of the subject that protrudes from a portion positioned therearound. Accordingly, the convex portion has only to be a portion of which even a part protrudes from a portion positioned therearound; and others, such as the size of the convex portion, the area of the convex portion, the heights and/or the number of protruding portions, and the continuity of a height or the like, do not matter.

Figure 8:
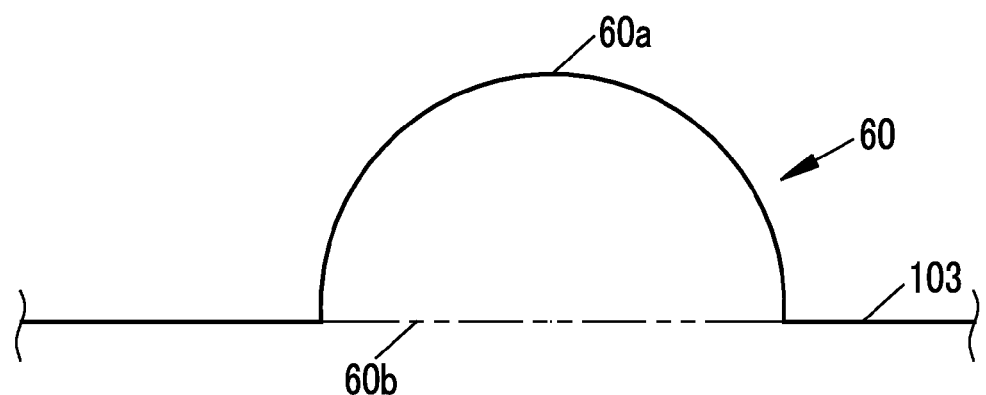
FIG. 8 is a diagram illustrating a convex portion as seen in a horizontal direction in a case where the height direction of the convex portion is set in parallel to a vertical direction.

More specifically, as shown in, for example, FIG. 8, a subject includes a polyp 60 as the convex portion. The polyp 60 has a shape where the polyp 60 protrudes from a portion of the subject positioned therearound. The polyp 60 includes an apex 60a and a flat portion 60b. FIG. 8 shows a case where the polyp 60 is seen in a horizontal direction in a case where the height direction of the polyp 60 is set in parallel to a vertical direction. However, since the polyp 60 is a three-dimensional structure, the polyp 60 is present not only on the front side of the plane of paper but also on the back side of the plane of paper. A flat surface which is formed by a flat portion of the subject positioned around the polyp 60 and on which the polyp 60 is formed is referred to as the flat portion 60b of the polyp 60. The flat surface formed by the flat portion positioned around the polyp 60 is an extended surface 103 of the flat portion 60b.

Figure 9:
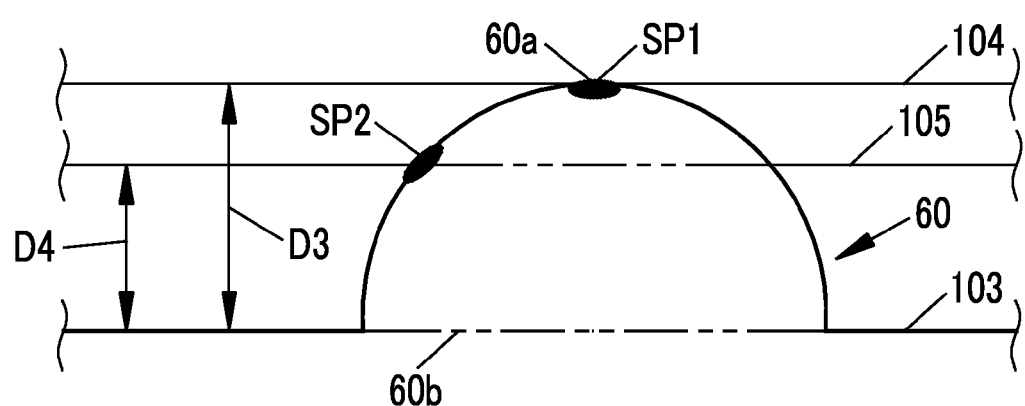
FIG. 9 is a diagram illustrating the height of the convex portion using a spot SP1 and a spot SP2.

Next, the height of the spot SP of the convex portion will be described. In this embodiment, the height of the spot SP of the polyp 60 is a distance between the spot SP of the polyp 60 and the flat portion 60b of the polyp 60 in the vertical direction. More specifically, a spot SP1 is formed at the apex 60a of the polyp 60 as shown in FIG. 9. Accordingly, in a case where a plane parallel to the extended surface 103 and passing through the apex 60a of the polyp 60 is referred to as a parallel plane 104, a distance between the parallel plane 104 and the extended surface 103 is a height D3 of the spot SP1 of the polyp 60. Therefore, the height D3 of the spot SP1 of the polyp 60 is a distance between the apex 60a of the polyp 60 and the flat portion 60b in the vertical direction. The polyp 60 and the height D3 are schematically shown, and the type, shape, size, and the like of the convex portion do not matter as long as the convex portion protrudes from portions positioned therearound.

Further, a spot SP2 is formed in a region except for the apex 60a of the polyp 60 in FIG. 9. That is, the spot SP2 is formed between the apex 60a of the polyp 60 and the end portion of the polyp 60. Accordingly, in a case where a plane parallel to the extended surface 103 and passing through the spot SP2 of the polyp 60 is referred to as a parallel plane 105, a distance between the parallel plane 105 and the extended surface 103 is a height D4 of the spot SP2 of the polyp 60. Therefore, the height D4 of the spot SP2 of the polyp 60 is a distance between the spot SP2 of the polyp 60 and the flat portion in the vertical direction.

Figure 10:
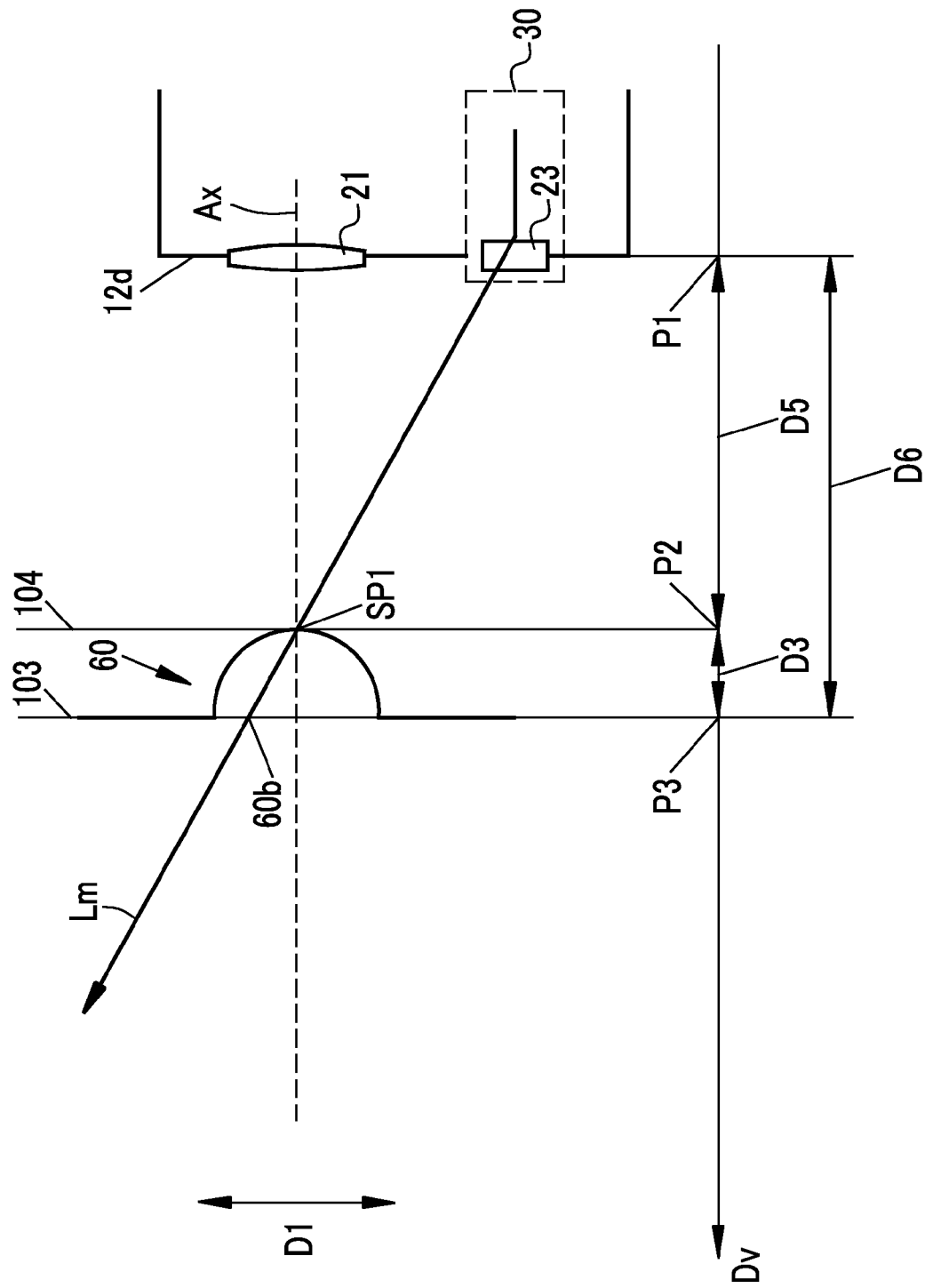
FIG. 10 is a diagram illustrating a relationship between the position of the spot SP1 and a subject.

An observation distance and the amount of offset will be described below. As shown in FIG. 10, the spot SP1 is formed at the apex 60a of the polyp 60 by auxiliary measurement light. An observation distance obtained from the spot SP1 is a distance D5 between a position P1 of the endoscope-distal end part 12d and a position P2 of the spot SP1. A measurement marker corresponding to the observation distance D5 is a measurement marker corresponding to actual measurement on the parallel plane 104. Accordingly, in a case where the spot SP1 is formed at the apex 60a of the polyp 60 and a measurement marker corresponding to the observation distance D5 is generated and displayed, a measurement marker corresponding to the actual measurement of a subject present on the parallel plane 104 is displayed. Therefore, a measurement marker of which gradations or the like are shifted to be larger than the actual measured value of a subject present on the extended surface 103 is displayed.

Then, the offset setting section 55 sets the height D3 of the spot SP1 of the polyp 60 as the amount of offset for the observation distance D5. After that, the offset distance-calculation section 56 calculates an offset distance D6 by adding the height D3 of the spot SP1 of the polyp 60, which is the amount of offset, to the observation distance D5.

Accordingly, the offset distance-calculation section 56 calculates the offset distance D6 by Equation (1) to be described below.

$$D6 = D5 + D3 \quad (1)$$

Next, the offset measurement marker-generation section 57 generates a measurement marker, which is based on the offset distance D6, as an offset measurement marker. More specifically, the offset measurement marker-generation section 57 refers to the marker table 54 and uses a measurement marker, which is obtained in a case where an observation distance is the distance D6, as an offset measurement marker. The offset measurement marker is to show an actual distance or size of a subject present on the extended surface 103.

In a case where an offset is not set or a case where the amount of offset is set to 0, the image processing section 52 does not set an offset on the basis of the position of the spot SP1 in the picked-up image or sets the amount of offset to 0 and generates a measurement marker showing the actual size of the subject. The image processing section 52 generates a measurement marker after calculating an appropriate size using an observation distance from the position of the spot SP1 as the distance D5 with reference to the marker table 54 in which a relationship between the position of the spot SP in the picked-up image and a measurement marker showing the actual size of a subject is stored. Accordingly, the image processing section 52 generates an offset measurement marker corresponding to the measurement marker that is obtained in a case where an observation distance is the distance D5.

The image processing section 52 generates a specific image by performing processing for superimposing the generated offset measurement marker on the picked-up image. For more accurate measurement, it is preferable that the offset measurement marker is superimposed to be displayed at a position where the spot SP is formed. Accordingly, in a case where the offset measurement marker is to be displayed at a position away from the spot SP, the offset measurement marker is displayed close to the spot SP as much as possible. The specific image in which the offset measurement marker is superimposed is displayed on the monitor 18 by the display control unit 40.

The functions of the image processing section 52 will be described in more detail using the picked-up image and the specific image. As shown in FIG. 11, an observation image CI1, a specific image MI1, and a specific image MI2 are compared. The observation image CI1, the specific image MI1, and the specific image MI2 are the picked-up images of the same subject including the polyp 60. The spot SP1 of the polyp 60 is formed at the apex 60a of the polyp 60. Further, the height of the polyp 60 is 2 mm.

Each of the observation image CI1, the specific image MI1, and the specific image MI2 includes the spot SP1 of which the position is specified at the position of a central coordinate (X2, Y2) among the coordinates of the picked-up image by the position specifying section 50. The radius of the spot SP1 is denoted by r2. The radius of the spot SP1 is calculated from the number of pixels of the spot SP1. The distance calculation section 51 determines the distance D5 as an observation distance using the central coordinate (X2, Y2) that is the position of the spot SP1. In this embodiment, the distance D5 that is an observation distance is 5 mm. An observation distance can be calculated from even the radius of the spot SP1. The observation image CH is an image in which a measurement marker is not displayed.

The specific image MI1 is an image that is obtained in a case where an offset is not set in the length measurement mode. In a case where an offset is not set, the specific image MI1 in which a measurement marker, which is obtained in a case where an observation distance is the distance D5 of 5 mm, is superimposed on the observation image CH is generated. This measurement marker MK1 has a diameter of 5 mm and has a circular-and-cruciform shape.

The specific image MI2 is an image that is obtained in a case where an offset is set in the length measurement mode. The height D3 of the spot SP1 is set as the amount of offset. The height D3 of the spot SP1 is 2 mm. Accordingly, the amount of offset of 2 mm is added to the distance D5 of 5 mm, so that the offset distance D6 is calculated as 7 mm. Therefore, a measurement marker obtained in a case where an observation distance is 7 mm is an offset measurement marker MK2. The specific image MI2 in which this offset measurement marker MK2 is superimposed on the observation image CH is generated. This offset measurement marker MK2 has a diameter of 5 mm and has a circular-and-cruciform shape.

In a case where an offset is set, it is possible to display a measurement marker closer to an actual distance by reducing an error even though a spot is formed at the convex portion of the subject as described above. The error causes the measured value, which is obtained using the measurement marker, of a distance on the subject, which refers to the offset measurement marker, to be smaller than an actual distance on the subject, or causes a size to be measured as a size smaller than an actual size on the subject. Accordingly, since the underestimation of the size of, for example, a polyp can be prevented, more appropriate diagnosis can be performed.

As shown in FIG. 12, an offset can be set to various observation distances. Specific images MI3, MI4, MI5, MI6, and MI7 are the picked-up images of the same subject including a polyp 62. Spots SP3, SP4, and SP5 of the polyp 62 are formed at an apex 62a of the polyp 62. Further, the height of the polyp 62 is 2 mm.

Each of the specific images MI3, MI4, and MI5 is a specific image in which an offset is not set, and each of the specific images MI6 and MI7 is a specific image in which an offset is set. The specific image MI3 includes a spot SP3, the central coordinate of the spot SP3 is (X1, Y1), the radius of the spot SP3 is denoted by r3, and the observation distance of the specific image MI3 is 5 mm Since an offset is not set in the specific image MI3, a measurement marker MK3 corresponding to the data of the specific image MI3 is displayed. The specific image MI4 includes a spot SP4, the central coordinate of the spot SP4 is (X2, Y2), the radius of the spot SP4 is denoted by r4, and the observation distance of the specific image MI4 is 7 mm Since an offset is not set in the specific image MI4, a measurement marker MK4 corresponding to the data of the specific image MI4 is displayed. The specific image MI5 includes a spot SP5, the central coordinate of the spot SP5 is (X3, Y3), the radius of the spot SP5 is denoted by r5, and the observation distance of the specific image MI5 is 9 mm Since an offset is not set in the specific image MI5, a measurement marker MK5 corresponding to the data of the specific image MI5 is displayed.

Further, the specific image MI6 includes a spot SP3, the central coordinate of the spot SP3 is (X2, Y2), the radius of the spot SP3 is denoted by r3, and the observation distance of the specific image MI6 is 5 mm. An offset is set in the specific image MI6. The amount of offset is 2 mm. Accordingly, the same marker as the measurement marker MK4 of the specific image MI4 of which the observation distance is 7 mm is displayed in the specific image MI6 as an offset measurement marker MK4.

Likewise, the specific image MI7 includes a spot SP4, the central coordinate of the spot SP4 is (X3, Y3), the radius of the spot SP4 is denoted by r4, and the observation distance of the specific image MI7 is 7 mm. An offset is set in the specific image MI7. The amount of offset is 2 mm. Accordingly, the same marker as the measurement marker MK5 of the specific image MI5 of which the observation distance is 9 mm is displayed in the specific image MI7 as an offset measurement marker MK5.

A case where the spot SP1 (see FIG. 9) is formed at the apex 60a of the polyp 60 by auxiliary measurement light has been described above. However, even in a case where the spot SP2 (see FIG. 9) is formed at a portion except for the apex 60a of the polyp 60, it is possible to display a measurement marker closer to the actual distance of a subject by setting the amount of offset in the same way as the case of the spot SP1.

Figure 13:
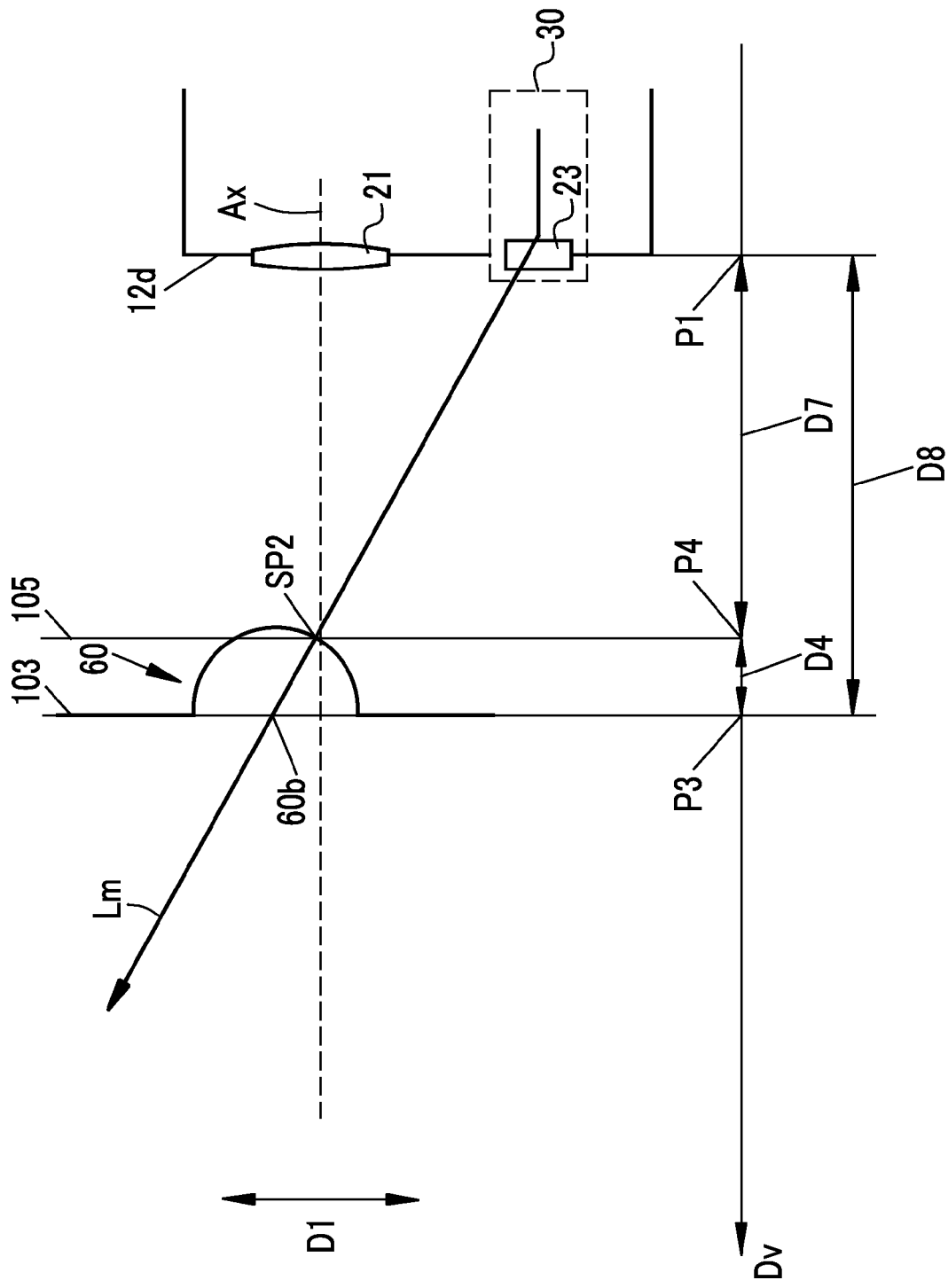
FIG. 13 is a diagram illustrating a relationship between the position of the spot SP1 and a subject.

For example, as shown in FIG. 13, a spot SP2 formed by auxiliary measurement light is formed between the apex 60a of the polyp 60 and an end portion of the polyp 60. An observation distance obtained from the spot SP2 is a distance D7 between a position P1 of the endoscope-distal end part 12d and a position P4 of the spot SP2. A measurement marker corresponding to the observation distance D7 is a measurement marker corresponding to actual measurement on a parallel plane 105. Accordingly, in a case where the spot SP2 is formed between the apex 60a of the polyp 60 and the end portion of the polyp 60 and a measurement marker corresponding to the observation distance D7 is generated and displayed, a measurement marker corresponding to the actual measurement of a subject present on the parallel plane 105 is displayed. Therefore, a measurement marker larger than actual measured size of a subject present on the extended surface 103 is displayed.

Then, the offset setting section 55 sets the height D4 of the spot SP2 of the polyp 60 as the amount of offset for the observation distance D7. After that, the offset distance-calculation section 56 calculates an offset distance D8 by adding the height D4 of the spot SP2 of the polyp 60, which is the amount of offset, to the observation distance D7. Accordingly, the offset distance-calculation section 56 calculates the offset distance D8 by Equation (2) to be described below.

$$D8=D7+D4 \qquad (2)$$

After that, even in the case of the spot SP2, an offset measurement marker showing the actual distance or size of a subject is generated in the same way as the case of the spot SP1.

According to the configuration of the invention, as described above, it is possible to simply measure the value of a distance or a size closer to an actual value by the offset measurement marker even in a case where a convex portion formed on the surface of a subject is irradiated with auxiliary measurement light. Further, since calibration does not need to be made for every convex portion, it is simple.

Figure 14:
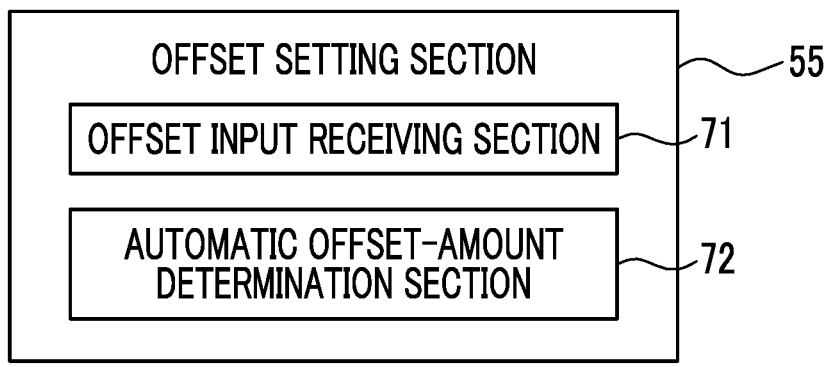
FIG. 14 is a block diagram showing the functions of an offset setting section.

As shown in FIG. 14, the offset setting section 55 may comprise an offset input receiving section 71 and an automatic offset-amount determination section 72. The offset input receiving section 71 receives the input of the amount of offset. The offset setting section 55 sets the amount of offset by using the input of the amount of offset that is received by the offset input receiving section 71.

The amount of offset may be manually or automatically input. In a case where the amount of offset is to be manually input, the amount of offset can be input using input means, such as the user interface 19. Accordingly, a user can manually input the amount of offset in, for example, a case where a subject including a polyp of which the height has been already known from an examination or the like performed until then is to be observed in the length measurement mode, a case where a subject including a polyp of which approximate size has been known from an image is to be observed in the length measurement mode, or the like.

Figure 15:
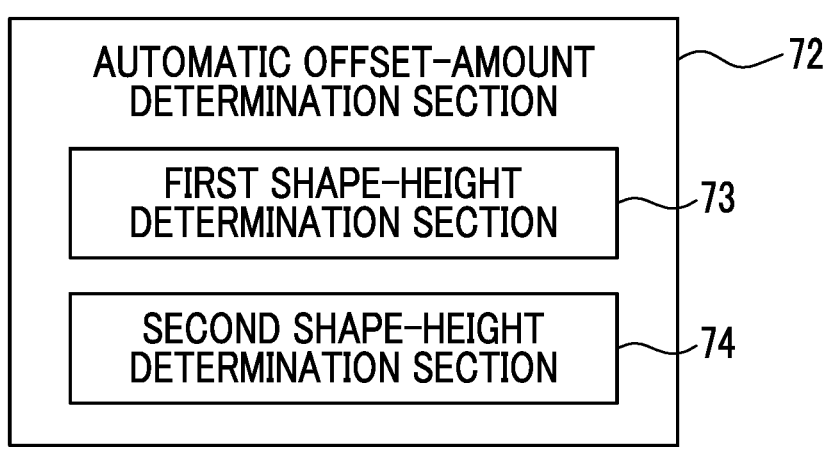
FIG. 15 is a block diagram showing the functions of an automatic offset-amount determination section.

In a case where the amount of offset is to be automatically input, the automatic offset-amount determination section 72 automatically determines the amount of offset. The offset setting section 55 sets the amount of offset by using the amount of offset that is determined by the automatic offset-amount determination section 72. The automatic offset-amount determination section 72 automatically determines the amount of offset by, for example, the image processing of an observation image. Specifically, the height of a convex portion of a subject may be calculated using, for example, light that forms a specific shape, such as a specific pattern, on the subject or a shadow that is formed on the subject by the convex portion of the subject. As shown in FIG. 15, the automatic offset-amount determination section 72 comprises a first shape-height determination section 73 and a second shape-height determination section 74.

A case where the height of an irradiated region of a convex portion of a subject is automatically determined using light that forms a specific shape, such as a specific pattern, on a subject will be described. The convex portion is a polyp 60. For example, light (specific light) that forms a linear specific region on a subject can be used as the light that forms a specific shape on a subject. Here, light that forms a spot in a case where a subject is irradiated with the light is used as auxiliary measurement light, but other light can be used. Accordingly, auxiliary measurement light forming the irradiated region can be used as specific light forming a specific region. In this case, the auxiliary measurement light-emitting unit 30 also functions as a specific light source unit. Accordingly, the auxiliary measurement light-emitting unit 30 emits auxiliary measurement light that forms a linear irradiated region on a subject.

Figure 16:
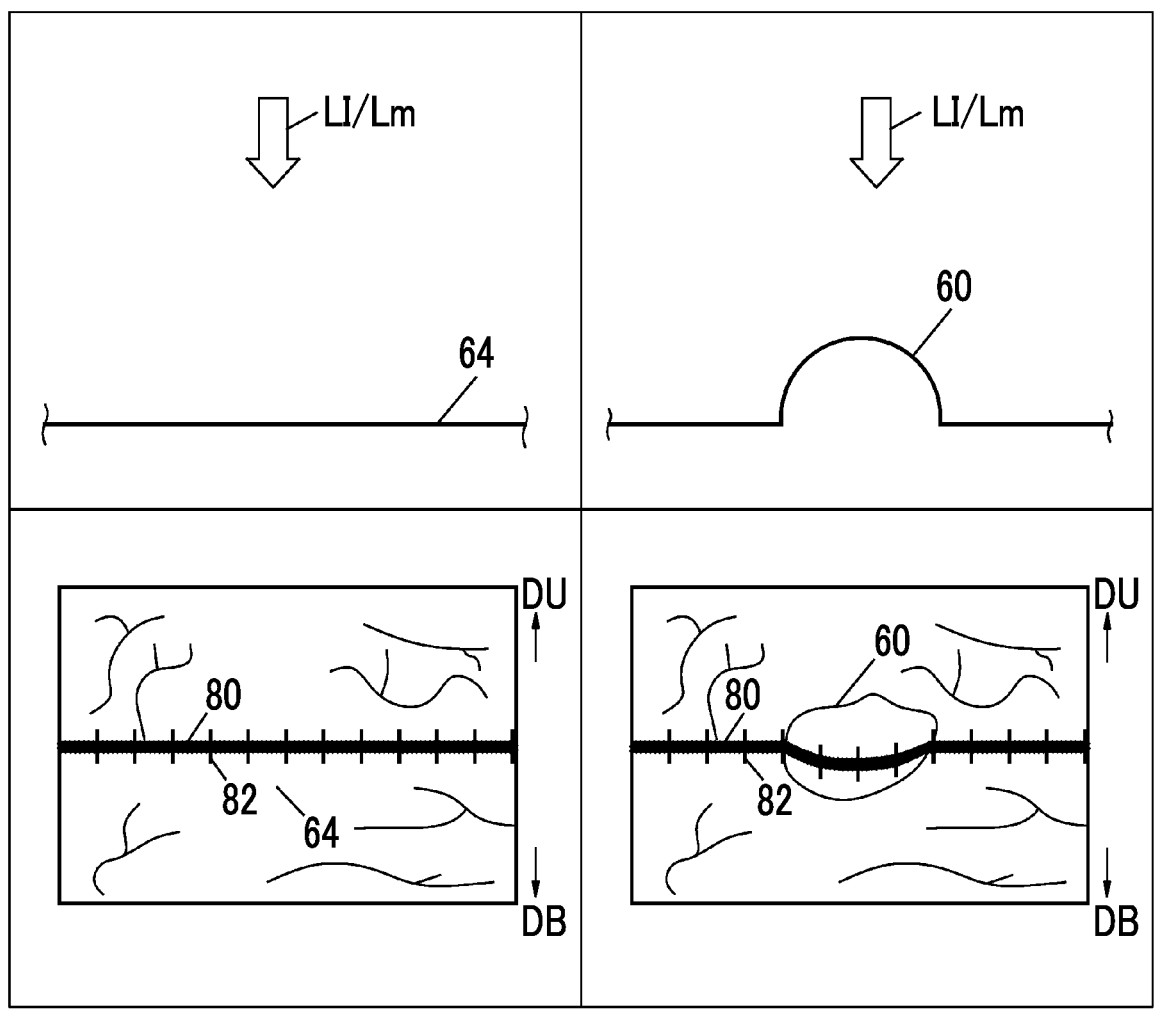
FIG. 16 is a table illustrating an image that is picked up using specific light.

The first shape-height determination section 73 specifies the irradiated region of the polyp 60 of the subject, and determines the height of the polyp 60 from the irradiated region of the polyp 60. More specifically, planar auxiliary measurement light forming a crossing line 80 on the subject as shown in FIG. 16 in a case where the subject is irradiated with, for example, auxiliary measurement light forming a linear irradiated region on the subject is used. In FIG. 16, the upper cells of a table show the shapes of subjects and the lower cells thereof show specific images. Further, the left column of the table corresponds to the case of a flat subject 64 and the right column thereof corresponds to the case of a subject including a polyp 60. Furthermore, in a case where a direction DU is set as an upward direction, a direction DB is a downward direction.

The crossing line 80 is formed in a linear shape on the subject 64 in a case where the polyp 60 is not formed. The crossing line 80 is formed in a shape including a curve in a case where the polyp 60 is formed. Further, the crossing line 80 is formed on the subject to be thicker in a case where an observation distance to the subject is shorter, and the crossing line 80 is formed on the subject to be thinner in a case where an observation distance to the subject is longer. Furthermore, a measurement marker formed of gradations 82 serving as an index of the height or size of the subject may be generated on the crossing line 80 as a measurement marker from the observation distance. Accordingly, an interval between the gradations 82 formed on the crossing line 80 formed on the subject is wider in a case where an observation distance to the subject is shorter, and an interval between the gradations 82 formed on the crossing line 80 formed on the subject is narrower in a case where an observation distance to the subject is longer. A relationship between the height of the polyp 60 and the shape (observation distance) of the crossing line 80 and/or measurement marker, such as the gradations 82, is obtained in advance from calibration using a subject that includes a polyp 60 of which the height is known. The height of an irradiated region of the polyp 60 can be automatically determined by the image analysis of a picked-up image.

A case where the height of a convex portion of a subject is automatically determined using a shadow formed on the subject by the convex portion of the subject will be described as another example. The convex portion is a polyp 60. For example, in a case where an irradiated region is positioned at an apex 60a (see FIG. 8) of the polyp 60 and a distance between the apex 60a of the polyp 60 and a flat portion 60b in a vertical direction is defined as a height, the height can be determined using a shadow that is formed by the polyp 60. A shadow may not be formed in some cases. However, in a case where a shadow is formed, the height can be determined using an observation distance and a dark portion of a picked-up image formed by the shadow.

Figure 17:
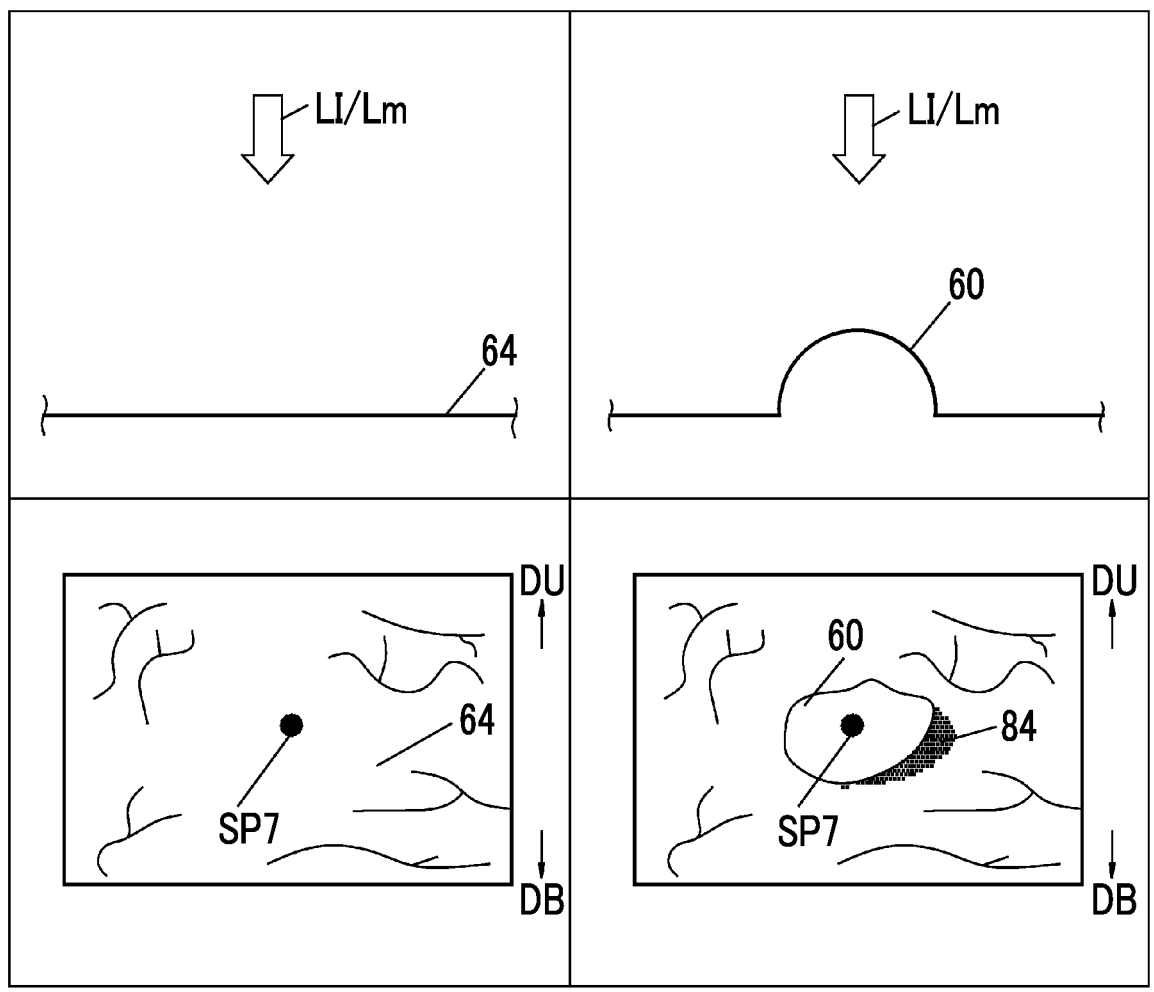
FIG. 17 is a table illustrating the shadow of a convex portion.

The second shape-height determination section 74 specifies the shadow of the polyp 60 by the image analysis using the picked-up image and determines the height of the polyp 60 from the shadow formed by the polyp 60. More specifically, for example, a shadow 84 is formed by the polyp 60 as shown in FIG. 17 in a case where the image of a subject is picked up. In a table shown in FIG. 17, upper cells show the shapes of subjects and lower cells show specific images. Further, a left column corresponds to the case of a flat subject 64 and a right column corresponds to the case of a subject including a polyp 60. Furthermore, in a case where a direction DU is set as an upward direction, a direction DB is a downward direction.

An observation distance is obtained from a spot SP7. Accordingly, a relationship among the area and the shape, such as the form, of a shadow, the height of a convex portion, and an observation distance is obtained in advance from calibration using a subject that includes a convex portion of which the height is known. The height of the convex portion can be automatically determined by the image analysis of a picked-up image.

In actual endoscopic diagnosis using the length measurement mode, a user inserts or extracts the endoscope 12 into or from a patient's body until the endoscope-distal end part 12d reaches the affected part of a patient. After the endoscope-distal end part 12d reaches the affected part, the amount of offset is set for the affected part and an offset measurement marker is positioned. The size of the affected part is measured using the offset measurement marker. A plan of treatment (extirpation or the like) for the affected part is determined depending on the result of diagnosis based on the size of the affected part.

Figure 18:
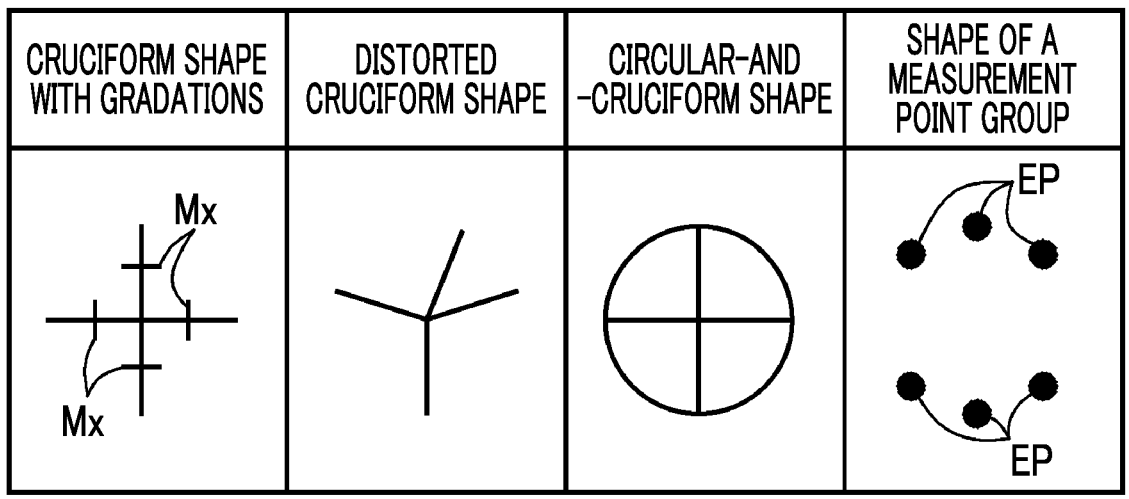
FIG. 18 is a diagram illustrating first measurement markers having a cruciform shape with gradations, a distorted cruciform shape, a circular-and-cruciform shape, and the shape of a measurement point group.

As in the above-mentioned embodiment, a first measurement marker corresponding to the actual size of the convex portion of the subject, which is 5 mm, may be displayed and the actual size of the subject may be set to any value (for example, 2 mm, 3 mm, 10 mm, or the like) according to an object to be observed or the purpose of observation. Further, in the above-mentioned embodiment, the first measurement marker has a cruciform shape where a vertical line and a horizontal line are orthogonal to each other. However, as shown in FIG. 18, the first measurement marker may have a cruciform shape with gradations where gradations Mx are given to at least one of a vertical line or a horizontal line of a cruciform shape. Furthermore, the first measurement marker may have a distorted cruciform shape of which at least one of a vertical line or a horizontal line is inclined. Moreover, the first measurement marker may have a circular-and-cruciform shape where a cruciform shape and a circle are combined with each other. In addition, the first measurement marker may have the shape of a measurement point group where a plurality of measurement points EP corresponding to an actual size from a spot display portion are combined with each other. Further, one first measurement marker may be displayed or a plurality of first measurement markers may be displayed, and the color of the first measurement marker may be changed according to an actual size.

Light that forms a spot as described above in a case where a subject is irradiated with the light is used as auxiliary measurement light, but other light may be used. For example, planar auxiliary measurement light that forms the crossing line 80 on a subject as shown in FIG. 16 in a case where the subject is irradiated with light may be used. In this case, a second measurement marker that includes the crossing line 80 and gradations 82 formed on the crossing line and serving as an index of the size of the subject (for example, a polyp) is generated as a measurement marker. In a case where planar auxiliary measurement light is used, the position specifying section 50 specifies the position of the crossing line 80(specific region). An observation distance is shorter as the crossing line 80 is positioned closer to the lower side in a screen downward direction DB, and an observation distance is longer as the crossing line 80 is positioned closer to the upper side in a screen upward direction DU. For this reason, an interval between the gradations 82 is larger as the crossing line 80 is positioned closer to the lower side in the screen downward direction DB, and an interval between the gradations 82 is smaller as the crossing line 80 is positioned closer to the upper side in the screen upward direction DU.

Figure 19:
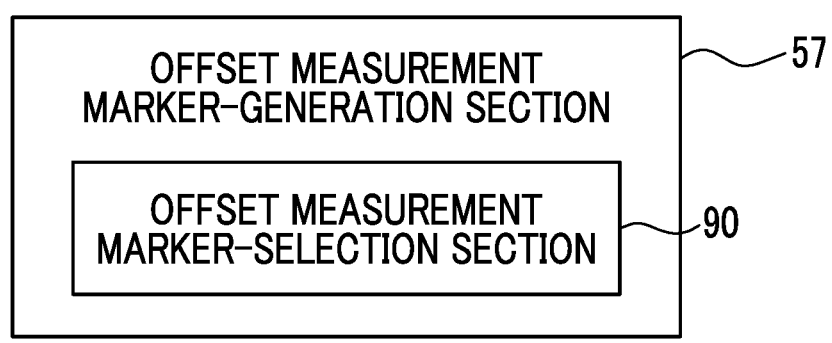
FIG. 19 is a block diagram showing the function of an offset measurement marker-generation section.

The selection of the type of an offset measurement marker may be received. More specifically, the offset measurement marker-generation section 57 may include an offset measurement marker-selection section 90 as shown in FIG. 19. The offset measurement marker-selection section 90 receives the selection of the type of an offset measurement marker. The offset measurement marker-selection section generates an offset measurement marker according to the selection of the type of an offset measurement marker.

A method of making the marker table 54 will be described below. A relationship between the position of a spot and the size of a marker can be obtained from the image pickup of a chart where a pattern having an actual size is regularly formed. For example, spot-like auxiliary measurement light is emitted to the chart; the image of a graph paper-shaped chart including lines (5 mm) having the same size as the actual size or lines (for example, 1 mm) having a size smaller than the actual size is picked up while an observation distance is changed to change the position of a spot; and a relationship between the position of a spot (pixel coordinates of the spot on the image pickup surface of the image pickup element 32) and the number of pixels corresponding to the actual size (pixels showing 5 mm that is the actual size) is acquired.

Figure 20:
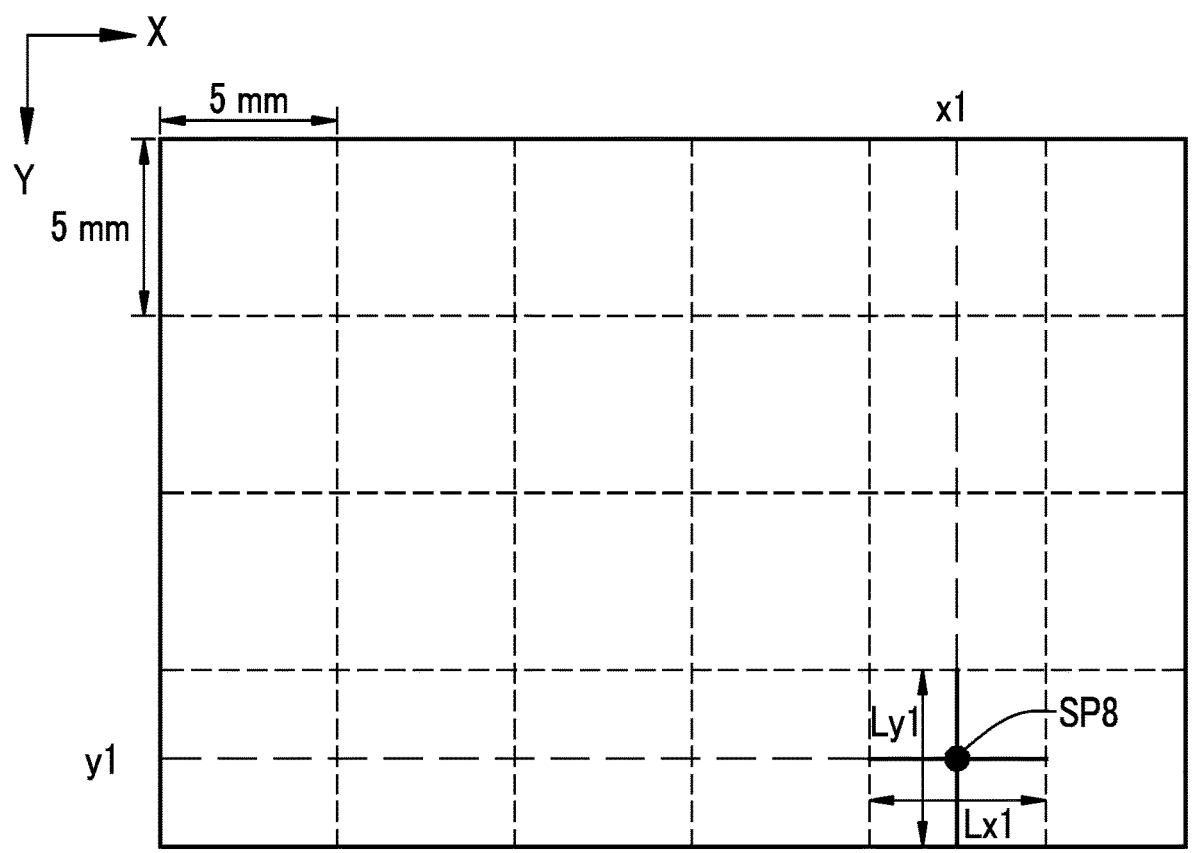
FIG. 20 is a diagram illustrating a graph paper-shaped chart that is used to measure a relationship between the position of a spot and the size of the first measurement marker in a case where an observation distance corresponds to the near end Px.
Figure 21:
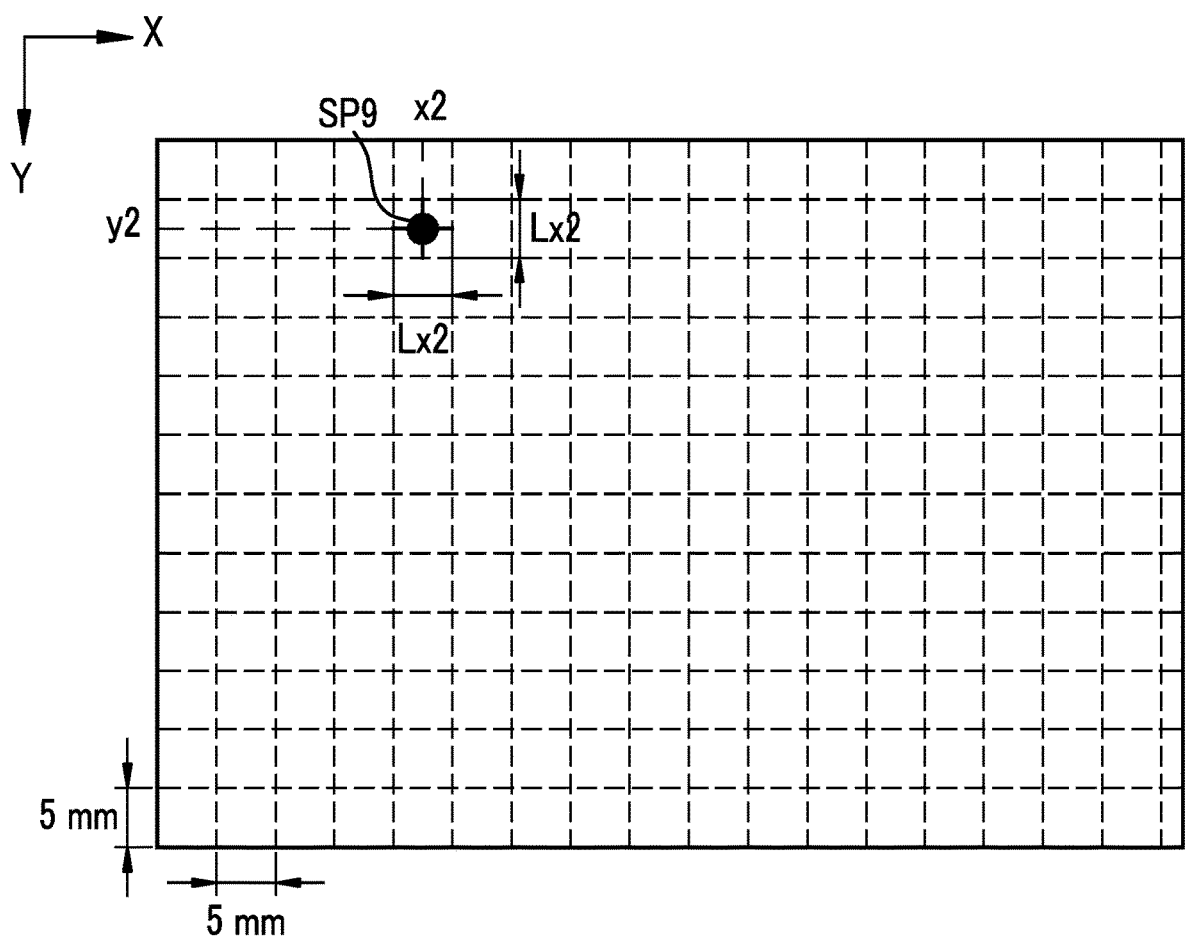
FIG. 21 is a diagram illustrating a graph paper-shaped chart that is used to measure a relationship between the position of a spot and the size of the first measurement marker in a case where an observation distance corresponds to the far end Py.

As shown in FIG. 20, (x1, y1) means the pixel position of a spot SP8 in an X direction and a Y direction on the image pickup surface of the image pickup element 32 (an upper left point is the origin of a coordinate system). The number of pixels in the X direction, which corresponds to the actual size of 5 mm, at the position (x1, y1) of the spot SP8 is denoted by Lx1, and the number of pixels in the Y direction is denoted by Ly1. This measurement is repeated while an observation distance is changed. FIG. 21 shows a state where the image of the chart including lines having a size of 5 mm as in FIG. 20 is picked up, but an interval between the lines is narrow since this state is a state where an observation distance is closer to the far end than that in the state of FIG. 20. The number of pixels in the X direction, which corresponds to the actual size of 5 mm, at the position (x2, y2) of a spot SP9 on the image pickup surface of the image pickup element 32 is denoted by Lx2, and the number of pixels in the Y direction is denoted by Ly2. Then, while an observation distance is changed, the same measurement as those in FIGS. 20 and 21 is repeated and the results thereof are plotted. The charts are shown in FIGS. 20 and 21 without consideration for the distortion of the objective lens 21.

Figure 22:
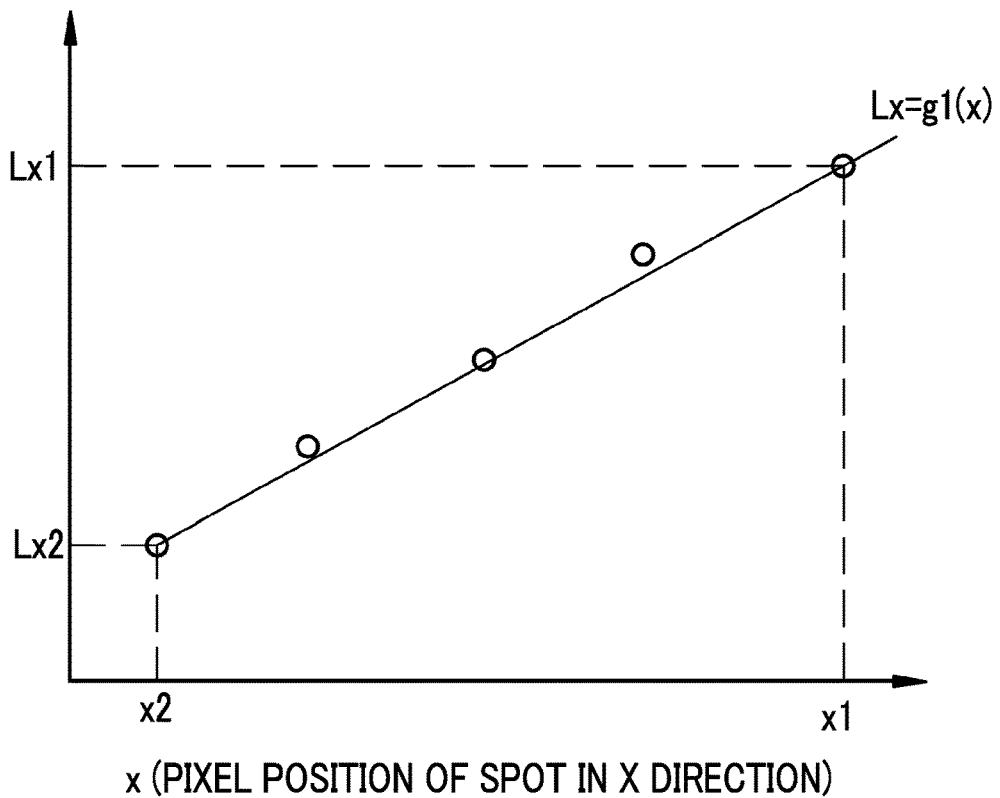
FIG. 22 is a graph showing a relationship between the pixel position of a spot in an X direction and the number of pixels of the first measurement marker in the X direction.
Figure 23:
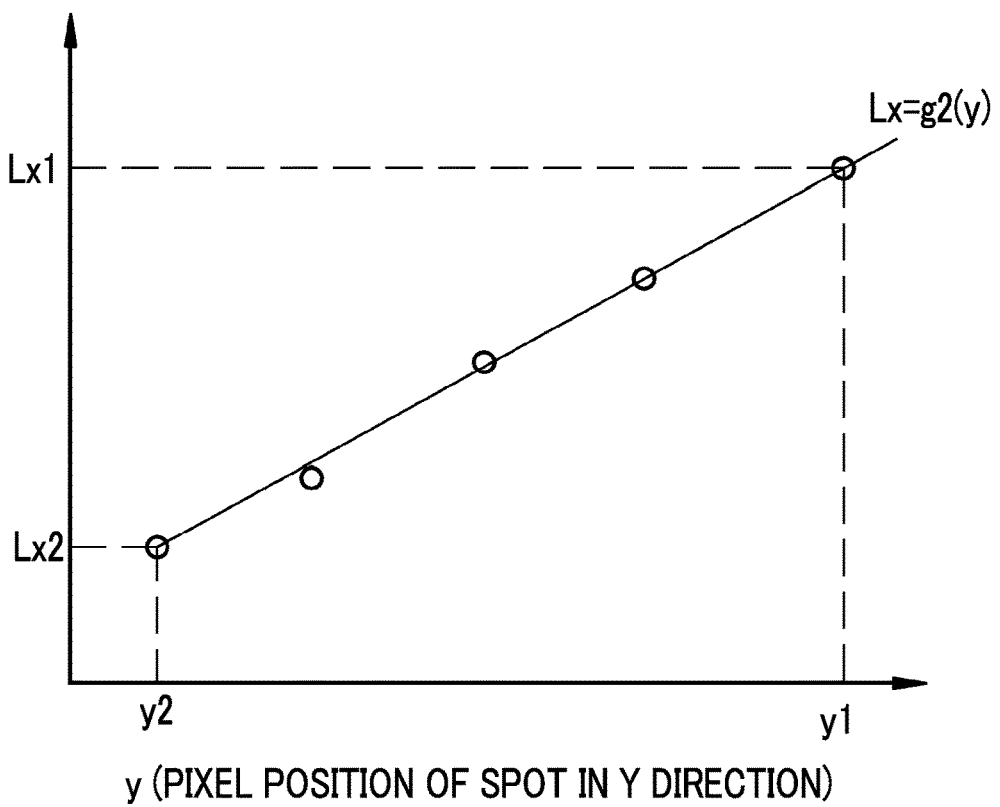
FIG. 23 is a graph showing a relationship between the pixel position of a spot in a Y direction and the number of pixels of the first measurement marker in the X direction.

FIG. 22 shows a relationship between the X-coordinate of the position of a spot and Lx (the number of pixels in the X direction), and FIG. 23 shows a relationship between the Y-coordinate of the position of a spot and Lx. Lx is expressed by "Lx=g1(x)" as a function of the position in the X direction from the relationship of FIG. 22, and Lx is expressed by "Lx=g2(y)" as a function of the position in the Y direction from the relationship of FIG. 23. The functions g1 and g2 can be obtained from the above-mentioned plotted results by, for example, a least-square method.

The X-coordinate of a spot corresponds to the Y-coordinate of a spot one to one, and basically the same results are obtained (the same number of pixels is obtained at the position of the same spot) even though any one of the function g1 or g2 is used. Accordingly, in a case where the size of the first measurement marker is to be calculated, any one of the function g1 or g2 may be used and a function of which sensitivity to a change in the number of pixels with respect to a change in position is higher may be selected from the functions g1 and g2. Further, in a case where the values of the functions g1 and g2 are significantly different from each other, it may be determined that "the position of a spot cannot be recognized".

Figure 24:
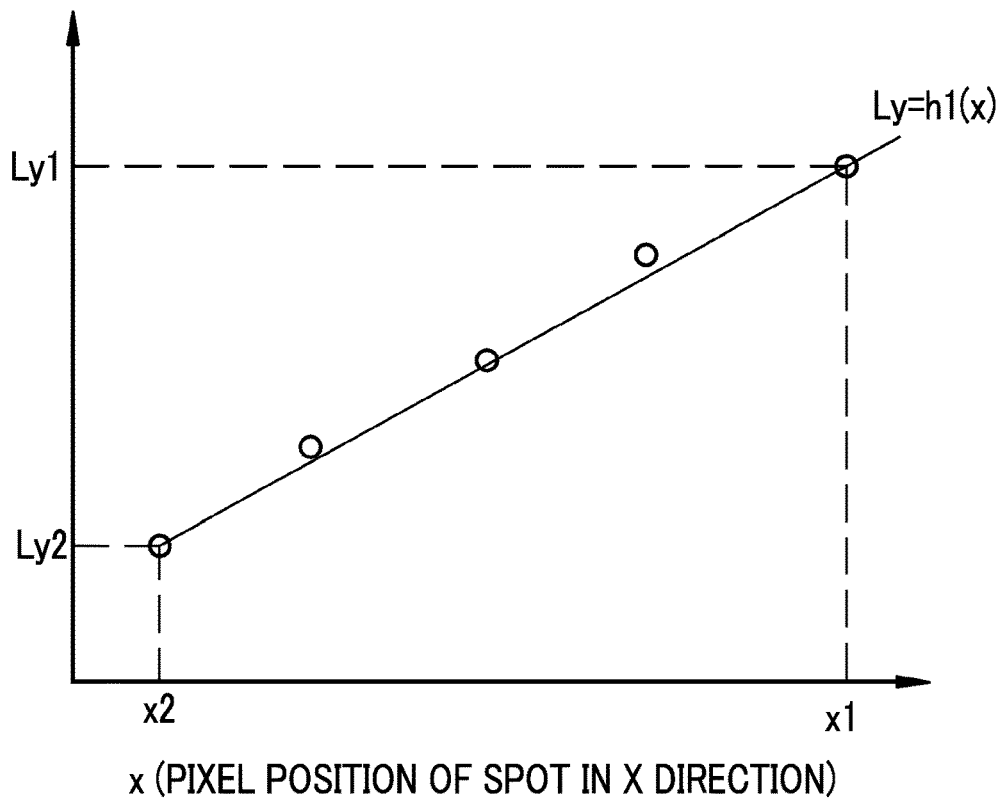
FIG. 24 is a graph showing a relationship between the pixel position of a spot in the X direction and the number of pixels of the first measurement marker in the Y direction.
Figure 25:
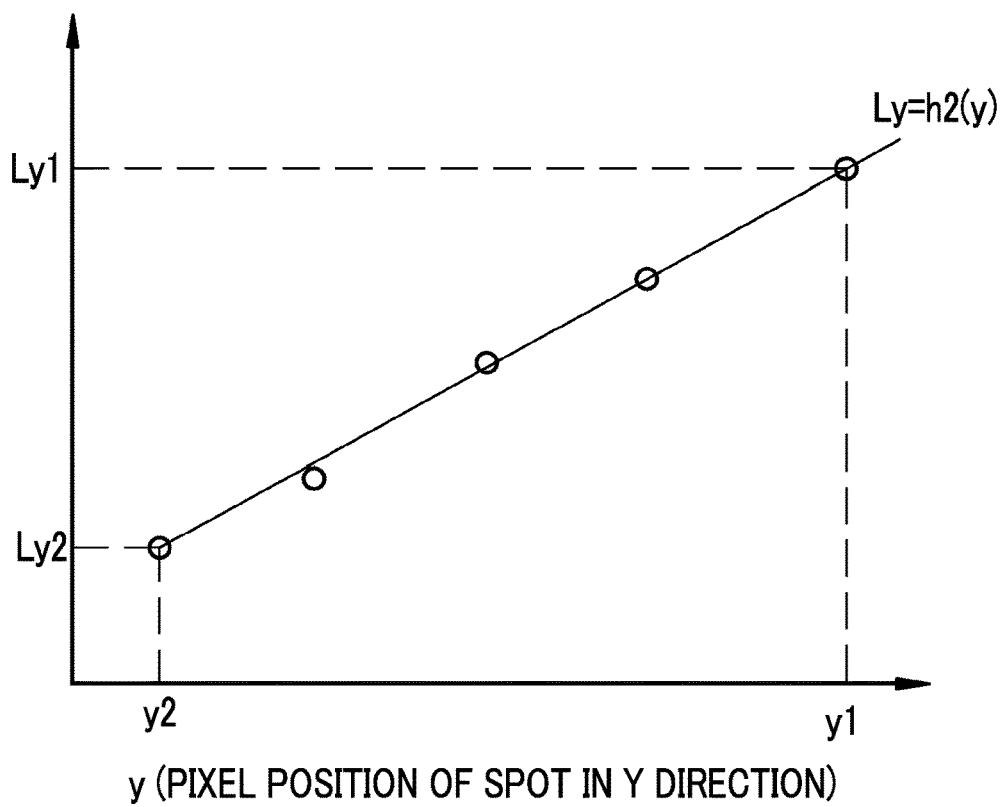
FIG. 25 is a graph showing a relationship between the pixel position of a spot in the Y direction and the number of pixels of the first measurement marker in the Y direction.

FIG. 24 shows a relationship between the X-coordinate of the position of a spot and Ly (the number of pixels in the Y direction), and FIG. 25 shows a relationship between the Y-coordinate of the position of a spot and Ly. Ly is expressed by "Ly=h1(x)" as the coordinate of the position in the X direction from the relationship of FIG. 24, and Ly is expressed by "Ly=h2(y)" as the coordinate of the position in the Y direction from the relationship of FIG. 25. Any one of the function h1 or h2 may also be used as Ly as in the case of Lx.

The functions g1, g2, h1, and h2 obtained as described above are stored in a marker table in the form of a look-up table. The functions g1 and g2 may be stored in the marker table 54 in the form of a function.

Figure 26:
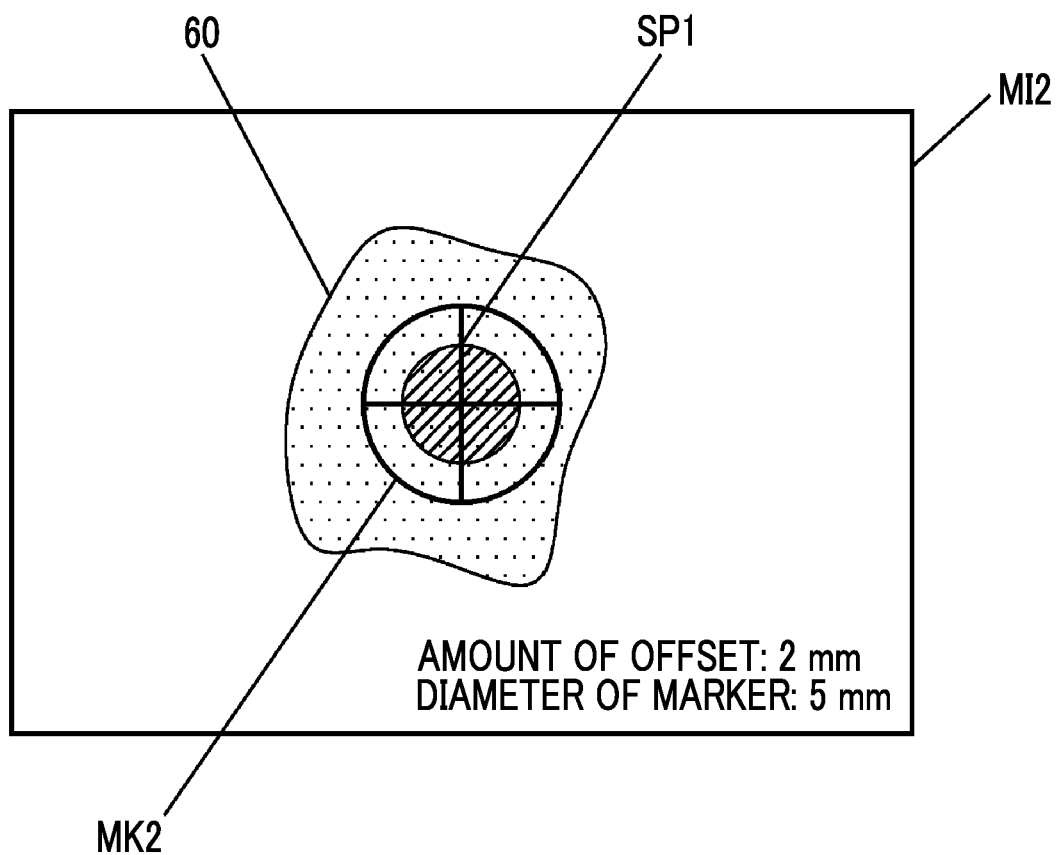
FIG. 26 is an image diagram of a specific image in which the amount of offset is displayed.

The specific image, which is formed as described above, is displayed on the monitor 18 by the display control unit 40. The monitor 18 may display the specific image and the amount of offset. The amount of offset may be displayed on the same screen or may be displayed on another screen. Further, the measurement marker and the gradations of the offset measurement marker may be displayed in addition to the amount of offset. More specifically, for example, as shown in FIG. 26, the amount of offset and the diameter of the measurement marker are displayed at the right lower portion or the like on the monitor 18 with characters.

Furthermore, a case where the spot SP1 (see FIG. 9) is formed at the apex 60a of the polyp 60 by auxiliary measurement light has been described above. However, even in a case where the spot SP1 (see FIG. 9) is formed not at the convex portion of the subject but at a concave portion of the subject, it is possible to display a measurement marker closer to an actual distance of a subject as in the case of the convex portion by setting the amount of offset to a negative value.

In the embodiment, the hardware structures of processing units, which perform various kinds of processing, such as the signal processing unit 39, the display control unit 40, and the system control unit 41, are various processors to be described later. Various processors include: a central processing unit (CPU) that is a general-purpose processor functioning as various processing units by executing software (program); a programmable logic device (PLD), which is a processor of which the circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope apparatus
12: endoscope
12a: insertion part
12b: operation part
12c: bendable part
12d: distal end part
12e: angle knob
13a: mode changeover switch
13b: freeze switch
14: light source device
16: processor device
18: monitor
19: user interface
21: objective lens
22: illumination lens
23: auxiliary measurement lens
24: opening
25: air/water supply nozzle 26: light source unit
27: light source control unit
28: light guide
29a: illumination optical system
29b: image pickup optical system
30: auxiliary measurement light-emitting unit
30a: light source
30b: DOE
30c: prism
32: image pickup element
33: image pickup control unit
34: CDS/AGC circuit
35: A/D converter
36: communication I/F
37: static image storage unit
38: communication I/F
39: signal processing unit
40: display control unit
50: position specifying section
51: distance calculation section
52: image processing section
53: image selection section
54: marker table
55: offset setting section
56: offset distance-calculation section
57: offset measurement marker-generation section
60, 62: polyp
60a: apex
60b: flat portion
64: subject
71: offset input receiving section
72: automatic offset-amount determination section
73: first shape-height determination section
74: second shape-height determination section
80: crossing line
82: gradations
84: shadow
90: offset measurement marker-selection section
101: solid line
102: dotted line
103: extended surface
104, 105: parallel plane
D1: first direction
D2: second direction
D3: height of spot SP1
D4: height of spot SP2
D5, D7: observation distance
D6, D8: offset distance
Dv: observation distance
DB: screen upward direction
DU: screen downward direction
Lm: optical axis of auxiliary measurement light
LI: illumination light
Ax: optical axis of objective lens
Rx: range of observation distance
Px: near end
Py: intermediate vicinity
Pz: far end
P1 to P5: position
Qx, Qy, Qz: image pickup range
SP, SP1 to SP9: spot
Lx1, Lx2: the number of pixels in X direction
Ly1, Ly2: the number of pixels in Y direction
CH: picked-up image
MI1 to MI7: specific image
MK1 to MK5: measurement marker or offset measurement marker
EP: measurement point
Mx: gradations

What is claimed is:

1. An endoscope apparatus comprising:
an illumination light source that emits illumination light used to illuminate a subject;
an auxiliary measurement light source that emits auxiliary measurement light; and
a processor coupled to a memory, the processor configured to:
acquire a picked-up image obtained from image pickup of the subject which is illuminated with the illumination light and on which an irradiated region is formed by the auxiliary measurement light;
specify a position of the irradiated region from the picked-up image;
obtain an observation distance, which is a distance between an endoscope-distal end part and the subject, from the position of the irradiated region;
set an amount of offset, which corresponds to a height of the irradiated region of a convex portion, for the observation distance;
calculate an offset distance by adding the amount of offset to the observation distance;
generate an offset measurement marker on the basis of the offset distance; and
cause a display to display a specific image in which the offset measurement marker is superimposed on the picked-up image.

2. The endoscope apparatus according to claim 1, wherein the height of the irradiated region of the convex portion is a distance between the irradiated region of the convex portion and a flat portion of the convex portion in a vertical direction.

3. The endoscope apparatus according to claim 1, wherein the processor is further configured to:
receive an input of the amount of offset, and
set the amount of offset by using the input of the received amount of offset.

4. The endoscope apparatus according to claim 3, wherein the amount of offset is manually input.

5. The endoscope apparatus according to claim 1, wherein the processor is further configured to:
automatically determine the amount of offset, and
set the amount of offset by using the determined amount of offset.

6. The endoscope apparatus according to claim 5, wherein:
specific light for forming a linear specific region is emitted on the subject; and
the processor is further configured to
specify the specific region of the convex portion of the subject and determine a height of the specific region of the convex portion from the specific region of the convex portion, and
determine the amount of offset by using the height of the specific region of the convex portion.

7. The endoscope apparatus according to claim 5, wherein a height of a specific region of the convex portion is a distance between an apex of the convex portion and a flat portion of the convex portion in a vertical direction,
the processor is further configured to
specify a shadow of the convex portion by image analysis using the picked-up image and determine a height of the convex portion from the shadow of the convex portion, and determine the amount of offset by using the height of the irradiated region of the convex portion.

8. The endoscope apparatus according to claim 1, wherein the processor generates a first offset measurement marker that shows an actual size of the subject or a second offset measurement marker that includes a crossing line formed on the subject by the auxiliary measurement light and gradations formed on the crossing line and serving as an index of a size of the subject.

9. The endoscope apparatus according to claim 8, wherein the processor is further configured to:
   receive selection of the type of the offset measurement marker, and
   generate the offset measurement marker according to the received selection.

10. The endoscope apparatus according to claim 1, further comprising:
   a display
   that displays the specific image and the amount of offset.

* * * * *